(12) United States Patent
Ramirez et al.

(10) Patent No.: US 11,975,325 B2
(45) Date of Patent: May 7, 2024

(54) NUCLEIC ACID CAPTURE, CONCENTRATION, AND PURIFICATION

(71) Applicant: ILLUMINA, INC., San Diego, CA (US)

(72) Inventors: Sean M. Ramirez, San Diego, CA (US); Anmiv Prabhu, San Diego, CA (US); Rigo Pantoja, San Diego, CA (US); Michelle Higgins, Carlsbad, CA (US)

(73) Assignee: Illumina, Inc., San Diego, CA (US)

( * ) Notice: Subject to any disclaimer, the term of this patent is extended or adjusted under 35 U.S.C. 154(b) by 237 days.

(21) Appl. No.: 17/358,783

(22) Filed: Jun. 25, 2021

(65) Prior Publication Data

US 2022/0001384 A1  Jan. 6, 2022

Related U.S. Application Data

(60) Provisional application No. 63/047,103, filed on Jul. 1, 2020.

(30) Foreign Application Priority Data

Jul. 17, 2020 (NL) ..................................... 2026080

(51) Int. Cl.
*C12Q 1/6813* (2018.01)
*B01L 3/00* (2006.01)
(Continued)

(52) U.S. Cl.
CPC ........... *B01L 3/502738* (2013.01); *B01L 7/00* (2013.01); *G01N 35/1097* (2013.01);
(Continued)

(58) Field of Classification Search
CPC .............. B01L 2300/0877; B01L 7/00; B01L 2300/0681; C12Q 2565/629; C12Q 2527/101
See application file for complete search history.

(56) References Cited

U.S. PATENT DOCUMENTS 6,706,499 B2   3/2004   Mansson et al.
9,340,828 B2   5/2016   Estmer Nilsson et al.
(Continued)

FOREIGN PATENT DOCUMENTS

CN   110958915 A   4/2020
GB   2461127 A   12/2009
(Continued)

OTHER PUBLICATIONS

Smith et al., "Simplified Low-Copy-Number DNA Analysis by Post-PCR Purification," J. Forensic Sci., July, vol. 52, No. 4, pp. 820-829. (Year: 2007).*
(Continued)

*Primary Examiner* — Young J Kim
(74) *Attorney, Agent, or Firm* — Dierker & Kavanaugh, P.C.

(57) ABSTRACT

An example of a kit includes a flow cell assembly. The flow cell assembly includes a reaction chamber, a temperature controlled flow channel in selective fluid communication with an inlet of the reaction chamber, and a filter positioned in the temperature controlled flow channel. The reaction chamber includes depressions separated by interstitial regions and capture primers attached within each of the depressions. The filter is i) to block concentrated biological sample-polymer complexes generated in the temperature controlled flow channel at a first temperature, and ii) to allow passage of concentrated biological sample and polymer released from the complexes in the temperature controlled flow channel at a second temperature.

16 Claims, 7 Drawing Sheets

(51) Int. Cl.
  *B01L 7/00*   (2006.01)
  *G01N 35/10*  (2006.01)

(52) U.S. Cl.
  CPC .............. *B01L 2300/0877* (2013.01); *B01L 2300/1805* (2013.01); *C12Q 1/6813* (2013.01)

(56) References Cited

U.S. PATENT DOCUMENTS

| | | |
|---|---|---|
| 9,587,268 B2 | 3/2017 | Borns |
| 9,730,637 B2 | 8/2017 | Simberg et al. |
| 10,093,962 B2 * | 10/2018 | Borns .................. C12Q 1/6832 |
| 2004/0094419 A1 | 5/2004 | Ueda et al. |
| 2017/0128947 A1 | 5/2017 | Lu et al. |
| 2019/0255505 A1 | 8/2019 | Rosenbaum et al. |

FOREIGN PATENT DOCUMENTS

| WO | WO-2005069737 A2 * | 8/2005 | ........ B01L 3/502715 |
|---|---|---|---|
| WO | WO-2007091281 A1 * | 8/2007 | ........ B01L 3/502715 |

OTHER PUBLICATIONS

Liu, W., et al., "A rapid temperature-responsive sol-gel reversible poly(N-isopropylacrylamide)-g-methylcellulose copolymer hydrogel", Biomaterials, vol. 25, No. 15, pp. 3005-3012, 2004.

* cited by examiner

NUCLEIC ACID CAPTURE, CONCENTRATION, AND PURIFICATION

CROSS-REFERENCE TO RELATED APPLICATIONS

This application claims the benefit of U.S. Provisional Application Ser. No. 63/047,103, filed Jul. 1, 2020, and Netherland Application Serial Number 2026080, filed Jul. 17, 2020; the content of each of which is incorporated by reference herein in its entirety.

BACKGROUND

Two classes of nucleic acids are found in living organisms (e.g., humans, animals, etc.), namely ribonucleic acid (RNA) and deoxyribonucleic acid (DNA). Both RNA and DNA can be grouped into different types, such as messenger RNA, ribosomal RNA, nuclear DNA, cytoplasmic DNA, etc. The various types of nucleic acids may be analyzed for a variety of purposes, such as research, diagnostics, forensics, genome sequencing, etc.

INTRODUCTION

A first aspect disclosed herein is a kit comprising a flow cell assembly including a reaction chamber having depressions separated by interstitial regions and capture primers attached within each of the depressions; a temperature controlled flow channel in selective fluid communication with an inlet of the reaction chamber; and a filter positioned in the temperature controlled flow channel, the filter i) to block concentrated deoxyribonucleic acid (DNA)-methyl cellulose complexes generated in the temperature controlled flow channel at a first temperature, and ii) to allow passage of concentrated DNA and methyl cellulose released from the complexes in the temperature controlled flow channel at a second temperature.

In an example of the first aspect, the kit further comprises a sample fluid including an aqueous carrier, a DNA sample, methyl cellulose, a polymer that is chemically inert to DNA hybridization, and a salt. In one example, the polymer that is chemically inert to DNA hybridization is selected from the group consisting of polyethylene glycol having a weight average molecular weight ranging from about 500 to less than about 200,000, polyvinyl pyrrolidone, polyvinyl alcohol, and combinations thereof. In another example, the DNA sample is present in the sample fluid at a first molar concentration ranging from about 1 pM (picoMolar) to about 1 mM; the methyl cellulose is present in the sample fluid in an amount ranging from about 0.5 wt % to about 20 wt % based on a total weight of the sample fluid; the polymer that is chemically inert to DNA hybridization is present in the sample fluid in an amount ranging from greater than 0 wt % to about 20 wt % based on the total weight of the sample fluid; and the salt is present in the sample fluid at a second molar concentration ranging from greater than 0 M to about 2 M.

In an example of the first aspect, the flow cell assembly further comprises a bypass line in fluid communication with an inlet of the temperature controlled flow channel and with an outlet of the temperature controlled flow channel; a first bypass valve to control flow of a sample fluid to the inlet of the temperature controlled flow channel; and a second bypass valve to control flow of the concentrated DNA and the methyl cellulose to the reaction chamber.

In an example of the first aspect, at least one surface of the temperature controlled flow channel includes a heating plate.

It is to be understood that any features of the first aspect disclosed herein may be combined together in any desirable manner and/or configuration to achieve the benefits as described in this disclosure, including, for example, capturing and concentrating DNA prior to analysis, processing, or the like.

A second aspect disclosed herein is a method comprising combining a DNA sample with a solution to form a sample fluid, the solution consisting of an aqueous carrier, methyl cellulose, a polymer that is chemically inert to DNA hybridization, and a salt, and the solution being at a temperature ranging from about 5° C. to about 30° C.; and heating the sample fluid to at least a gelation temperature of the methyl cellulose, thereby forming DNA-methyl cellulose complexes in the aqueous carrier.

In an example of the second aspect, the method further comprises cooling the sample fluid to below the gelation temperature of the methyl cellulose, thereby detangling the DNA-methyl cellulose complexes to release the DNA sample and the methyl cellulose.

In another example of the second aspect, the method further comprises increasing a concentration of the salt in the solution, thereby lowering the gelation temperature of the methyl cellulose.

In an example of the second aspect, the DNA sample includes cell-free DNA, library DNA, whole genome amplified DNA, or combinations thereof.

In an example of the second aspect, the DNA sample includes a plurality of differently sized DNA inserts including small DNA inserts and large DNA inserts; at least some of the large DNA inserts are entangled in the DNA-methyl cellulose complexes; at least some of the small DNA inserts are not entangled in the DNA-methyl cellulose complexes; and the method further comprises performing a purification process after heating to separate the at least some of the small DNA inserts from the DNA-methyl cellulose complexes. In an example, the purification process involves filtering, centrifuging, decanting, or combinations thereof. In another example, the method further comprises cooling the DNA-methyl cellulose complexes to below the gelation temperature of the methyl cellulose, thereby detangling the DNA-methyl cellulose complexes to release the at least some of the large DNA inserts and the methyl cellulose.

It is to be understood that any features of the second aspect may be combined together in any desirable manner. Moreover, it is to be understood that any combination of features of the first aspect and/or of the second aspect may be used together, and/or may be combined with any of the examples disclosed herein to achieve the benefits as described in this disclosure, including, for example, capturing DNA and/or purifying DNA.

A third aspect disclosed herein is a method comprising introducing a sample fluid to a temperature controlled flow channel having a filter positioned therein, the sample fluid including an aqueous carrier, a DNA sample, methyl cellulose, a polymer that is chemically inert to DNA hybridization, and a salt; heating the temperature controlled flow channel as the sample fluid is introduced such that a temperature of the sample fluid contained therein is increased to at least a gelation temperature of the methyl cellulose, thereby forming DNA-methyl cellulose complexes in the temperature controlled flow channel; continuing a flow of the sample fluid through the temperature controlled flow channel as the temperature controlled flow channel is heated, thereby concentrating a plurality of the DNA-methyl cellulose complexes at the filter in the temperature controlled flow channel; and cooling the temperature controlled flow channel such that a temperature of the sample fluid contained therein is decreased to below the gelation temperature of the methyl cellulose, thereby detangling the concentrated DNA-methyl cellulose complexes to release the DNA sample and the methyl cellulose, whereby the DNA sample and the methyl cellulose are able to pass through the filter.

In an example of the third aspect, the method further comprises selecting a heating temperature for the temperature controlled flow channel in accordance with a concentration of the salt in the sample fluid.

In another example of the third aspect, the method further comprises transporting the DNA sample and the methyl cellulose from the temperature controlled flow channel to a flow cell.

It is to be understood that any features of the third aspect may be combined together in any desirable manner. Moreover, it is to be understood that any combination of features of the first aspect and/or of the second aspect and/or of the third aspect may be used together, and/or may be combined with any of the examples disclosed herein to achieve the benefits as described in this disclosure, including, for example, concentrating DNA prior to analysis, processing, or the like.

A fourth aspect disclosed herein is a method comprising introducing a sample fluid to a flow cell, the sample fluid including an aqueous carrier, a DNA sample, methyl cellulose, a polymer that is chemically inert to DNA hybridization, and a salt; and the flow cell including a reaction chamber having depressions separated by interstitial regions and capture primers attached within each of the depressions; initiating seeding and hybridization of at least some of the DNA sample in at least some of the depressions; heating the flow cell such that a temperature of the sample fluid contained therein is increased to at least a gelation temperature of the methyl cellulose, thereby forming DNA-methyl cellulose complexes with unbound DNA sample; introducing an additional amount of the sample fluid to the flow cell; cooling the flow cell such that the temperature of the sample fluid contained therein is decreased to below the gelation temperature of the methyl cellulose, thereby detangling the concentrated DNA-methyl cellulose complexes to release the DNA sample and the methyl cellulose; and initiating seeding and hybridization of at least some of the released DNA sample and the DNA sample from the additional sample fluid in at least some of the depressions.

In an example of the fourth aspect, the method further comprises selecting a heating temperature for the flow cell in accordance with a concentration of the salt in the sample fluid.

It is to be understood that any features of the fourth aspect may be combined together in any desirable manner. Moreover, it is to be understood that any combination of features of the first aspect and/or of the second aspect and/or of the third aspect and/or of the fourth aspect may be used together, and/or may be combined with any of the examples disclosed herein to achieve the benefits as described in this disclosure, including, for example, improving DNA seeding on a flow cell surface.

A fifth aspect disclosed herein is a kit comprising a sample fluid consisting of an aqueous carrier; a deoxyribonucleic acid (DNA) sample; methyl cellulose; a polymer that is chemically inert to DNA hybridization; and a salt or solvent to adjust a gelation temperature of the methyl cellulose.

In an example of the fifth aspect, the DNA sample is present in the sample fluid at a first molar concentration ranging from about 1 pM to about 1 mM; the methyl cellulose is present in the sample fluid in an amount ranging from about 0.5 wt % to about 20 wt % based on a total weight of the sample fluid; the polymer that is chemically inert to DNA hybridization is present in the sample fluid in an amount ranging from greater than 0 wt % to about 20 wt % based on a total weight of the sample fluid; and the sample fluid includes the salt, and the salt is present in the sample fluid at a second molar concentration ranging from greater than 0 M to about 2 M.

In an example of the fifth aspect, the kit further comprises a flow cell assembly including a temperature controlled flow channel to receive the sample fluid; a reaction chamber having depressions separated by interstitial regions, capture primers attached within each of the depressions, and an inlet in selective fluid communication with the temperature controlled flow channel; and a filter positioned in the temperature controlled flow channel, the filter i) to block concentrated DNA sample-methyl cellulose complexes generated in the temperature controlled flow channel when the sample fluid is exposed to a first temperature, and ii) to allow passage of concentrated DNA sample and methyl cellulose released from the complexes in the temperature controlled flow channel at a second temperature.

It is to be understood that any features of the fifth aspect may be combined together in any desirable manner. Moreover, it is to be understood that any combination of features of the first aspect and/or of the second aspect and/or of the third aspect and/or of the fourth aspect may be used together, and/or of the fifth aspect may be used together, and/or may be combined with any of the examples disclosed herein to achieve the benefits as described in this disclosure, including, for example, improving DNA seeding on a flow cell surface.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
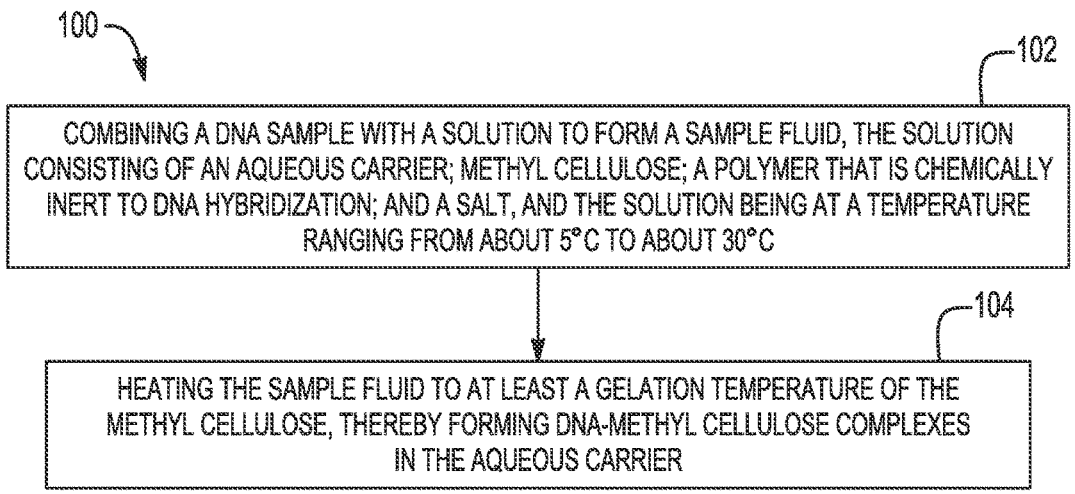
FIG. 1 is a flow diagram illustrating an example of a method for deoxyribonucleic acid (DNA) capture.

DNA can be used in a variety of applications, such as replication and sequencing. Some sequencing systems utilize relatively low DNA loading inputs in order to output high quality data. It is desirable, therefore, to minimize DNA sample loss. The examples disclosed herein capture and concentrate DNA in order to maximize the DNA loading available for purification, seeding, etc. More specifically, the examples disclosed herein utilize a thermally reversible precipitating polymer, methyl cellulose, as a complexing agent for the DNA. Under controlled temperature conditions, the methyl cellulose either forms a complex with the DNA or releases the DNA from the complex. The methods disclosed herein utilize the methyl cellulose-DNA complex for DNA capture, concentration, purification, and/or seeding.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

The term "adapter", as used herein, refers to a linear oligonucleotide sequence that can be fused to a nucleic acid molecule, for example, by ligation or tagmentation. Suitable adapter lengths may range from about 10 bases to about 100 bases, or from about 12 bases to about 60 bases, or from about 15 bases to about 50 bases. The adapter may include any combination of nucleotides and/or nucleic acids. In some examples, the adapter can include a sequence that is complementary to at least a portion of a primer, for example, a primer including a universal nucleotide sequence (such as a P5 or P7 sequence). In some examples, the adapter can include a sequencing primer sequence or sequencing binding site. Combinations of different adapters may be incorporated into a nucleic acid molecule, such as a DNA fragment.

As used herein, "cell-free DNA" (cfDNA) refers to DNA or RNA that is not contained within cells. As examples, cfDNA may be cell-free fetal DNA or cell-free tumor DNA. Cell-free fetal DNA is the DNA or RNA of a fetus that is circulating freely in the maternal blood stream. Cell-free tumor DNA is tumor-derived fragmented DNA (i.e., circulating tumor DNA or ctDNA). The examples disclosed herein may also be suitable for capturing, concentrating, etc. viral DNA and/or bacterial DNA.

The term "complementary DNA" (cDNA), as used herein, refers to DNA synthesized from a single-stranded RNA template, e.g., in a reaction catalyzed by the enzyme reverse transcriptase.

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a substrate having a surface opening that is at least partially surrounded by interstitial region(s) of the substrate. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

As used herein, the term "DNA insert" refers to a DNA fragment in a sample. The size of the DNA can range from about one hundred bases or base pairs to one hundred million bases or base pairs, or more. DNA inserts in any given sample may have a size distribution ranging from small to large. Small DNA inserts generally refer to DNA fragments having from about 100 bases or base pairs to about 1,000 bases or base pairs (e.g., 100, 200, 300, 400, 500, 600, 700, 800, 900, 1000, or any number in between). Large DNA inserts generally refer to DNA fragments having more than 1,000 bases or base pairs (e.g., 1200, 1300, 1500, 2000, 3000, 3500, 4000, 4500, 5000, 5500, 6000, 6500, 7000, 7,500, 8000, 8500, 9000, 9500, 10,000, 10,500, 11,000, 11,500, 12,000, 12500, 13000, 14000, 14500, 15000, 15500, 16000, 16500, 17000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,500, 30,000, 30,500, 31,000, 31,500, 32,000, 33,000, 34,000, 35,000, 36,000, 37,000, 38,000, 39,000, 40,000, 42,000, 45,000, 50,000, 55,000, 60,000, 65,000, 70,000, 75,000, 80,000, 85,000, 90,000, 95,000, 100,000, 110,000, 120,000, 130,000, 140,000, 150,000, 160,000, 170,000, 180, 000, 200,000, 225,000, 250,000, 300,000, 350,000, 400,000, 450,000, 500,000, 550,000, 600,000, 650,000, 700,000, 750, 000, 800,000, 850,000, 900,000, 1,000,000, 1,250,000, 1,500,000, 2,000,000, 2,500,000, 3,000,000, 4,000,000, 5,000,000, 6,000,000, 7,000,000, 8,000,000, 9,000,000, 10,000,000, 15,000,000, 20,000,000, 30,000,000, 40,000,000, 50,000,000, 75,000,000, 100,000,000, or more, or any number in between).

As used herein, the terms "fluid communication" and "fluidly connected" refer to two spatial regions being connected together such that a liquid or gas may flow between the two spatial regions. For example, a temperature control flow channel may be in fluid communication with a reaction chamber such that a fluid may flow freely or in a controlled manner into the reaction chamber from the temperature control flow channel. The terms "in fluid communication" or "fluidly connected" allow for two spatial regions being in fluid communication through one or more valves, restrictors, or other fluidic components that are configured to control or regulate a flow of fluid through a system.

The term "flow cell" refers to a vessel having a chamber where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like.

A "fragment", as used herein, refers to a portion or piece of genetic DNA material.

Also as used herein, "genomic DNA" (gDNA) and "whole genome amplified DNA" refer to high molecular weight (>1000 base pairs (bp)) chromosomal DNA.

As used herein, "library DNA" refers to a collection of DNA fragments that include adapters at both ends. In some examples, the DNA fragments may be fragments of gDNA or cDNA.

A "nucleotide," as used herein, includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (the nucleotides of RNA), the sugar is a ribose, and in deoxyribonucleotides (the nucleotides of DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. As examples, the phosphate groups may be in the mono-, di-, tri-, tetra-, penta-, or hexa-phosphate form. These nucleotides are natural nucleotides, but it is to be further understood that non-natural nucleotides, modified nucleotides or analogs of the aforementioned nucleotides can also be used.

As used herein, the phrase "polymer that is chemically inert to DNA hybridization" refers to a polymer that will not participate in or otherwise interfere with hybridization of DNA.

Also as used herein, the term "primer" refers to a nucleic acid molecule that can hybridize to a target sequence, such as an adapter attached to a DNA fragment. As one example, an amplification primer can serve as a starting point for template amplification and cluster generation. As another example, a synthesized nucleic acid (template) strand may include a site to which a primer (e.g., a sequencing primer) can hybridize in order to prime synthesis of a new strand that is complementary to the synthesized nucleic acid strand. Any primer can include any combination of nucleotides or analogs thereof. In some examples, the primer is a single-stranded oligonucleotide or polynucleotide. The primer length can be any number of bases long and can include a variety of natural or non-natural nucleotides. In an example, the sequencing primer is a short strand, ranging from 10 bases to 60 bases, or from 20 bases to 40 bases.

A "reaction chamber" refers to an area in a flow cell where a reaction can be carried out. The reaction chamber may include depressions where sequencing chemistry (e.g., amplification primers) is immobilized.

As used herein, a "temperature controlled flow channel" is an enclosed area through which a liquid sample can flow and that is capable of being heated or cooled by an internal component (e.g., a heating plate) or an external component (e.g., a laser).

The aspects and examples set forth herein and recited in the claims can be understood in view of the above definitions.

Sample Fluid

In any of the examples disclosed herein, a sample fluid is used. The sample fluid includes a DNA sample in a solution of an aqueous carrier, methyl cellulose, a polymer that is chemically inert to DNA hybridization, and a salt or solvent to adjust a gelation temperature of the methyl cellulose. In some examples, the solution consists of the aqueous carrier, methyl cellulose, the polymer that is chemically inert to DNA hybridization, and the salt or solvent to adjust the gelation temperature of the methyl cellulose. In one example, the sample fluid includes the DNA sample in a solution of the aqueous carrier, methyl cellulose, the polymer that is chemically inert to DNA hybridization, and the salt.

The DNA sample may include cell-free DNA, library DNA, whole genome amplified DNA, or combinations thereof. The DNA sample may be single stranded or double stranded DNA, depending upon the application in which the sample fluid is to be used. For example, single stranded DNA may be included in a sample fluid to be used in a sequencing application, and single or double stranded DNA may be included in a sample fluid that is to be purified.

In an example, the DNA sample is present in the sample fluid at a molar concentration ranging from about 1 pM to about 1 mM (1000 µM). In other examples, the DNA sample is present in the sample fluid at a molar concentration ranging from about 10 pM to about 950 µM, for example from about 25 pM to about 750 µM, from about 500 pM to about 500 nM, from about 500 nM to about 500 µM, etc.

The aqueous carrier in the solution may be water, a salt solution, or a buffer solution (e.g., a weak acid and one of its salts (conjugate base) or a weak base and one of its salts (conjugate acid). Example buffer solutions include a tris (hydroxymethyl)aminomethane hydrochloride (TRIS-HCl) buffer, a tris(hydroxymethyl)aminomethane (TRIS) buffer, or a saline sodium citrate (SSC) buffer. The aqueous carrier makes up a balance of the sample fluid, and thus the amount may vary depending upon the amounts of the other components.

Methyl cellulose is a thermally reversible hydrogel that precipitates or gels in an aqueous solution with thermal exposure. As an example, methyl cellulose is commercially available under the tradename METHOCEL® from Dow Chemical Co. In an example, the lower critical solution temperature (LCST) transition range of the methyl cellulose ranges from about 25° C. to about 60° C., which may depend upon the grade of the methyl cellulose and/or the concentration of the methyl cellulose in the sample fluid. Other factors, such as the pH of the solution, may also affect the LCST. Additionally, when the concentration is higher, the LCST is more measurable than when the concentration is lower. The salt in the sample fluid may alter the LCST transition range. For example, an increased salt concentration can force the methyl cellulose to precipitate out at lower temperatures. For example, when the salt concentration ranges from about 1.5 M to about 2 M, the LCST transition range of the methyl cellulose ranges from about 5° C. to about 45° C. Below the LCST, the methyl cellulose is dissolved in the aqueous carrier, and at or above the LCST, the methyl cellulose precipitates out of the aqueous carrier. This behavior is reversible, and thus the methyl cellulose can be controllably switched between the dissolved and precipitated states.

In an example, the methyl cellulose is present in the sample fluid in an amount ranging from about 0.5 wt % to about 20 wt %, based on the total weight of the sample fluid. In another example, the methyl cellulose is present in the sample fluid in an amount ranging from about 1 wt % to about 15 wt %, based on the total weight of the sample fluid, e.g., from about 1.5 wt % to about 10 wt %, from about 5 wt % to about 7.5 wt %, etc.

The sample fluid also includes the polymer that is chemically inert to DNA hybridization. In the examples disclosed herein, the polymer that is chemically inert to DNA hybridization is selected from the group consisting of polyethylene glycol having a weight average molecular weight (g/mol or Daltons) ranging from about 500 to less than about 200,000, polyvinyl pyrrolidone, polyvinyl alcohol, and combinations thereof. Unlike the methyl cellulose, the chemically inert polymer does not precipitate out of the sample fluid with thermal exposure.

In an example, the chemically inert polymer is present in the sample fluid in an amount ranging from greater than 0 wt % to about 20 wt %, based on the total weight of the sample fluid. In another example, the chemically inert polymer is present in the sample fluid in an amount ranging from about 0.5 wt % to about 18 wt %, based on the total weight of the sample fluid, e.g., from about 1.5 wt % to about 16 wt %, from about 5 wt % to about 15 wt %, etc.

The sample fluid also includes the salt or the solvent, which may be included to adjust a gelation temperature of the methyl cellulose. If a salt solution or a buffer solution is used as the aqueous solution, an additional salt or solvent may or may not be added. Examples of suitable salts include sodium chloride (NaCl), sodium bromide (NaBr), and sodium iodide (NaI). In one example, salts containing potassium, calcium, magnesium, or ammonium cations may be used. In another example, salts containing carbonate, sulfate, phosphate, or nitrate anions may be used. In another example, a solvent, such as ethylene glycol, propylene glycol, and/or glycerol may be used to shift the gelation temperature.

In an example, the total salt concentration in the sample fluid ranges from greater than 0 M to about 2 M. In other examples, the salt is present in the sample fluid at a molar concentration ranging from about 0.25 M to about 1.75 M, for example from about 0.5 M to about 1.5 M, from about 1 M to about 2 M, from about 0.1 M to about 1 M, etc.

When making the sample fluid, the solution may be prepared by mixing together the aqueous carrier, the methyl cellulose, the chemically inert polymer, and the salt or solvent. The temperature of the solution may be maintained below the precipitation/gelation temperature of the methyl cellulose. This helps to prevent premature precipitation of the methyl cellulose, and can also prevent any salt from crashing out of solution. The DNA sample may be added to the solution to form the sample fluid. Some examples of the method disclosed herein may include increasing a concentration of the salt or the amount of solvent in the solution, thereby lowering the gelation temperature of the methyl cellulose.

Any example of the sample fluid may be included in a kit. The components of the kit may depend upon the application in which the sample fluid will be used. For example, the kit may include a flow cell when the sample fluid is to be used in sequencing.

Several example methods are described herein which utilize an example of the sample fluid. The sample fluids discussed in relation to the methods specifically mention the salt. It is to be understood however, that any example of the sample fluid disclosed herein (e.g., including the solvent instead of the salt) may be used in any example of the method disclosed herein.

DNA Capture

An example of a DNA capture method 100 is shown in FIG. 1. The method 100 includes combining a DNA sample with a solution to form a sample fluid, the solution consisting of an aqueous carrier, methyl cellulose, a polymer that is chemically inert to DNA hybridization, and a salt, and the solution being at a temperature ranging from about 5° C. to about 30° C. (reference numeral 102); and heating the sample fluid to at least a gelation temperature of the methyl cellulose, thereby forming DNA-methyl cellulose complexes in the aqueous carrier (reference numeral 104). It is to be understood that any example of the sample fluid may be used in the DNA capture method 100.

Figure 2:
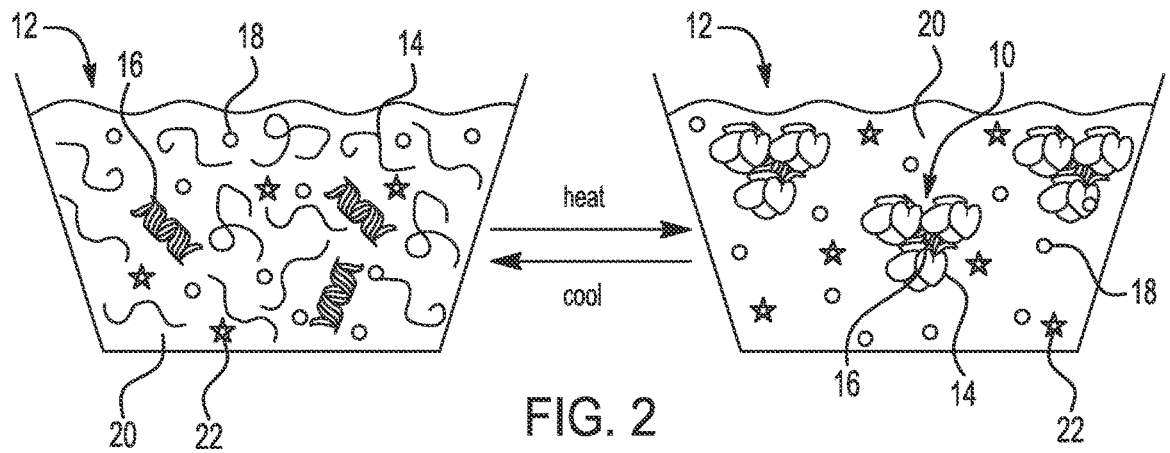
FIG. 2 is a schematic illustration of the method of FIG. 1.

The method 100 is shown schematically in FIG. 2. The sample fluid 12 at the left side of the arrows in FIG. 2 is below the gelation temperature of the methyl cellulose 14. At this temperature, the methyl cellulose 14, the chemically inert polymer 18, and the salt 22 are dissolved in the aqueous carrier 20. The salt 22 in the aqueous carrier 20 reduces the methyl cellulose solubility and helps reduce DNA charge interactions, thus inducing the DNA to adhere to the precipitated methyl cellulose.

The sample fluid 12 at the right side of the arrows in FIG. 2 is at or above the gelation temperature of the methyl cellulose 14. At this temperature, the chemically inert polymer 18 and the salt 22 remain dissolved in the aqueous carrier 20. The methyl cellulose 14, however, precipitates out of solution. The precipitated methyl cellulose polymer chains physically interact with the DNA sample 16 to form DNA-methyl cellulose complexes 10. The DNA molecules become entangled in the precipitated methyl cellulose polymer chains. The interaction between the DNA molecules and the methyl cellulose polymer chains is non-covalent.

The temperature to which the sample fluid 12 is heated depends upon the gelation temperature of the methyl cellulose 14. The gelation temperature of the methyl cellulose 14 depends, in part, upon the concentration of the methyl cellulose 14 in the sample fluid 12. As such, some examples of the method 100 may involve selecting a heating temperature in accordance with a concentration of the methyl cellulose 14 in the sample fluid 12. Generally, the temperature to which the sample fluid 12 is heated ranges from about 25° C. to about 60° C. As one specific example, when the methyl cellulose concentration ranges from about 1 wt % to about 6 wt %, the heating temperature ranges from about 40° C. to about 60° C. As another specific example, when the methyl cellulose concentration ranges from about 5 wt % to about 12 wt %, the heating temperature ranges from about 25° C. to about 50° C. As described herein, the gelation temperature of the methyl cellulose 14 may also depend upon the concentration of the salt 22 in the sample fluid 12. As such, some examples of the method 100 may involve selecting a heating temperature in accordance with a concentration of the salt in the sample fluid. As one specific example, when the salt concentration ranges from about 0.5 M to about 1.5 M, the heating temperature ranges from about 40° C. to about 60° C. As another specific example, when the salt concentration ranges from about 1.8 M to about 2 M, the heating temperature ranges from about 5° C. to about 60° C.

Heating may be performed using any suitable heat source, which may be an internal component of the fluidic device that contains the sample fluid 12, or may be an external component that is not part of the fluidic device that contains the sample fluid. An example of an internal component may include a heating plate that is integrated into a flow channel (see, e.g., FIG. 5B). Examples of external components include a heating plate upon which a fluidic device is placed, or a laser that is directed toward the fluidic device.

The duration for which the sample fluid 12 is heated depends upon the application for which the method 100 is performed. For example, if the method 100 is used to capture and concentrate the DNA sample in a particular area of a flow channel, heating may be performed until a desirable amount of sample fluid is introduced into the flow channel.

If or when it is desirable to release the DNA captured in the DNA-methyl cellulose complexes 10, the method 100 may further include cooling the sample fluid 12 to below the gelation temperature of the methyl cellulose 14, thereby detangling the DNA-methyl cellulose complexes 10 to release the DNA sample 16 and the methyl cellulose 14. Below the gelation temperature, the methyl cellulose 14, the chemically inert polymer 18, and the salt 22 are dissolved in the aqueous carrier 20.

In some examples, cooling is passive as the sample fluid 12 is allowed to cool to room temperature on its own. Alternatively, cooling may be performed using any suitable cooling source, which may be an internal component of the fluidic device that contains the sample fluid 12, or may be an external component that is not part of the fluidic device that contains the sample fluid. An example of an internal component may include a thermoelectric cooler that is integrated into a flow channel or a reaction chamber. Examples of external components include a fan that is directed toward the fluidic device.

As schematically illustrated in FIG. 2, the methyl cellulose 14 acts as a DNA capturing agent or a DNA releasing agent, depending upon the temperature to which the sample fluid 12 is exposed. This may be desirable for a variety of applications, including DNA capture, purification, or concentration.

DNA Purification

An example of the DNA capture method 100 may be used for DNA capture and purification. In one example, a purification method may be desirable when the DNA sample in the sample fluid 12 includes a plurality of differently sized DNA inserts including small DNA inserts and large DNA inserts. In an example, the DNA inserts are single stranded DNA inserts. When a plurality of differently sized DNA inserts are present in the sample fluid 12, the larger DNA inserts tend to interact with the precipitated methyl cellulose polymer chains more than the smaller DNA inserts. As such, at least some of the large DNA inserts are entangled in the DNA-methyl cellulose complexes 10, and at least some of the small DNA inserts are not entangled in the DNA-methyl cellulose complexes 10. This may be due to the size of the larger DNA inserts, which can physically obstruct the smaller DNA inserts from becoming entangled with the precipitated methyl cellulose polymer chains.

Figure 3:
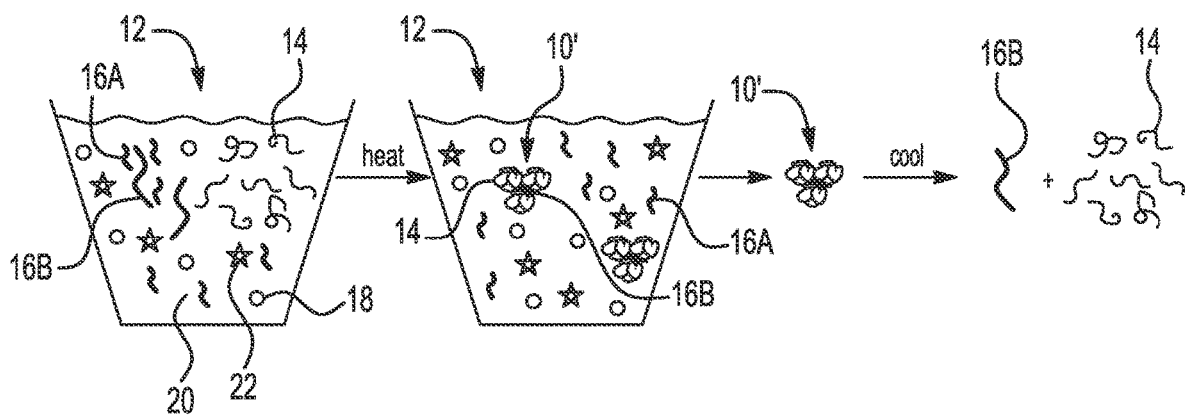
FIG. 3 is a schematic illustration of another example of a method involving the method of FIG. 1 and purification.

An example of the purification method is shown schematically in FIG. 3. This example of the method includes combining a DNA sample, which includes both small DNA inserts 16A and large DNA inserts 16B, with a solution to form a sample fluid 12; heating the sample fluid 12 to at least a gelation temperature of the methyl cellulose 14, thereby forming large DNA insert-polymer complexes 10' in the aqueous carrier 20; and performing a purification process after heating to separate the at least some of the small DNA inserts 16A from the large DNA insert-polymer complexes 10'.

The sample fluid 12 at the far left in FIG. 3 is below the gelation temperature of the methyl cellulose 14. At this temperature, the methyl cellulose 14, the chemically inert polymer 18, and the salt 22 are dissolved in the aqueous carrier 20. The small DNA inserts 16A and the large DNA inserts 16B are dispersed in the aqueous carrier 20.

When heated to at least the gelation temperature of the methyl cellulose 14, the chemically inert polymer 18 and the salt 22 remain dissolved in the aqueous carrier 20, while the methyl cellulose 14 precipitates out of solution. The precipitated methyl cellulose polymer chains physically interact with at least some of the large DNA inserts 16B to form the large DNA insert-polymer complexes 10'. At least some of the smaller DNA inserts 16A are not entangled with the methyl cellulose polymer chains, and thus are not part of the large DNA insert-polymer complexes 10'.

The sample fluid 12, having the large DNA insert-polymer complexes 10' and the free small DNA inserts 16A therein, may then be exposed to a purification process. The purification process may involve filtering, centrifuging, decanting, or combinations thereof. Filtration may be used to separate the large DNA insert-polymer complexes 10' from the small DNA inserts 16A fluid and the aqueous carrier 20 (and any components dissolved therein). Centrifugation may be used to separate the large DNA insert-polymer complexes 10' from the small DNA inserts 16A. In any instances where liquid and small DNA inserts 16A are separated from the large DNA insert-polymer complexes 10' in the same container, decantation may be used to remove the aqueous carrier 20, any components dissolved therein, and the small DNA inserts 16A. In one example, centrifugation may be followed by decantation.

Fresh solution (without additional DNA sample) may be added to the separated complexes 10' prior to cooling to release the large DNA inserts 16B. If or when it is desirable to release the large DNA inserts 16B captured in the DNA-methyl cellulose complexes 10', this example may further include cooling the DNA-methyl cellulose complexes 10' to below the gelation temperature of the methyl cellulose 14, thereby detangling the complexes 10' to release the large DNA inserts 16B and the methyl cellulose 14. Below the gelation temperature, the methyl cellulose 14, the chemically inert polymer 18, and the salt 22 are dissolved in the aqueous carrier 20.

Concentrating DNA

Figure 4:
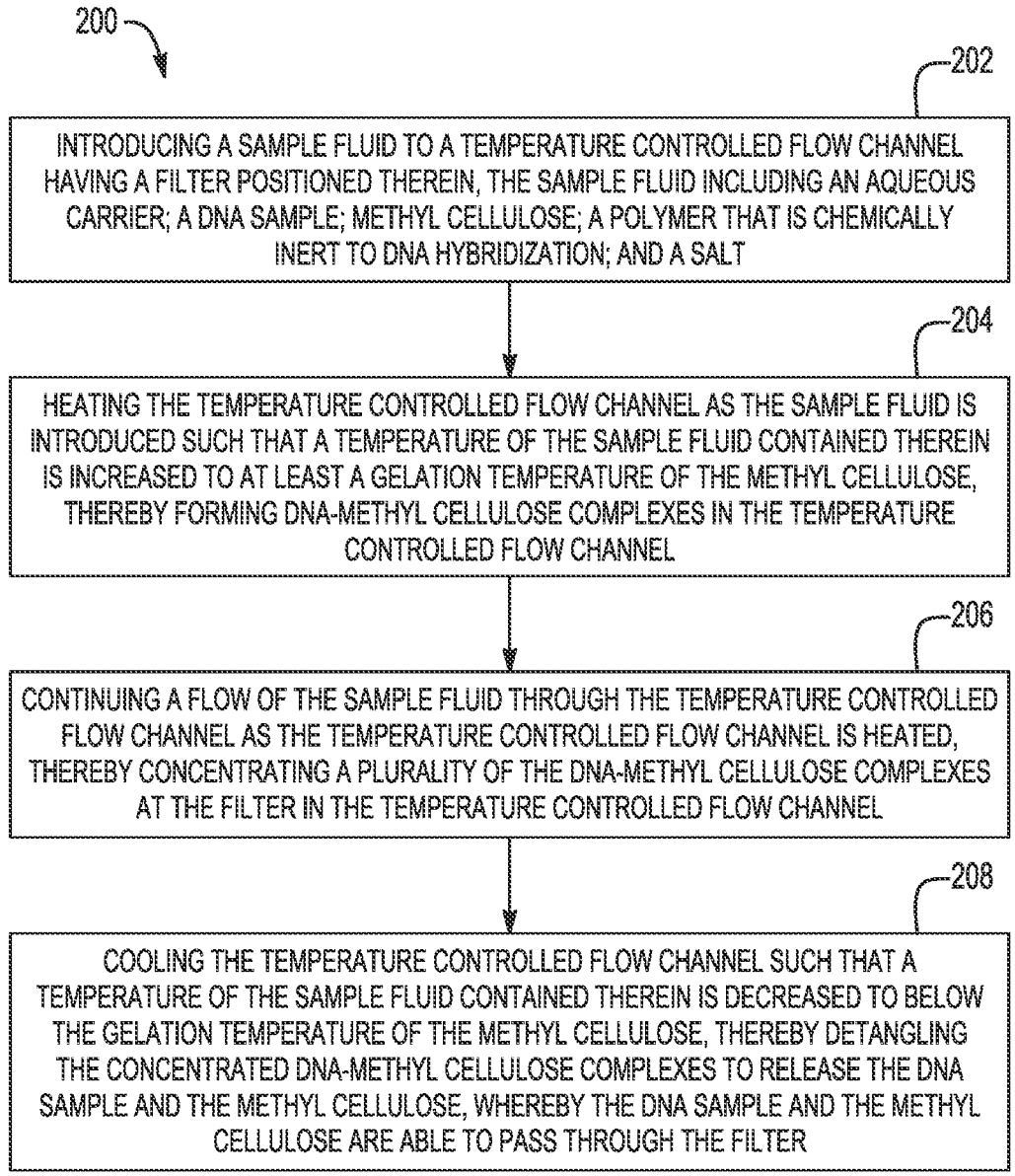
FIG. 4 is a flow diagram illustrating an example of a method for DNA concentration.

Another example method is shown at reference numeral 200 in FIG. 4. This example method 200 may be used for DNA capture and concentration. The method 200 includes introducing a sample fluid to a temperature controlled flow channel having a filter positioned therein, the sample fluid including an aqueous carrier, a DNA sample, methyl cellulose, a polymer that is chemically inert to DNA hybridization, and a salt (reference numeral 202); heating the temperature controlled flow channel as the sample fluid is introduced such that a temperature of the sample fluid contained therein is increased to at least a gelation temperature of the methyl cellulose, thereby forming DNA-methyl cellulose complexes in the temperature controlled flow channel (reference numeral 204); continuing a flow of the sample fluid through the temperature controlled flow channel as the temperature controlled flow channel is heated, thereby concentrating a plurality of the DNA-methyl cellulose complexes at the filter in the temperature controlled flow channel (reference numeral 206); and cooling the temperature controlled flow channel such that a temperature of the sample fluid contained therein is decreased to below the gelation temperature of the methyl cellulose, thereby detangling the concentrated DNA-methyl cellulose complexes to release the DNA sample and the methyl cellulose, whereby the DNA sample and the methyl cellulose are able to pass through the filter (reference numeral 208).

The method 200 is shown schematically in FIG. 5A through 5E.

Figure 5:
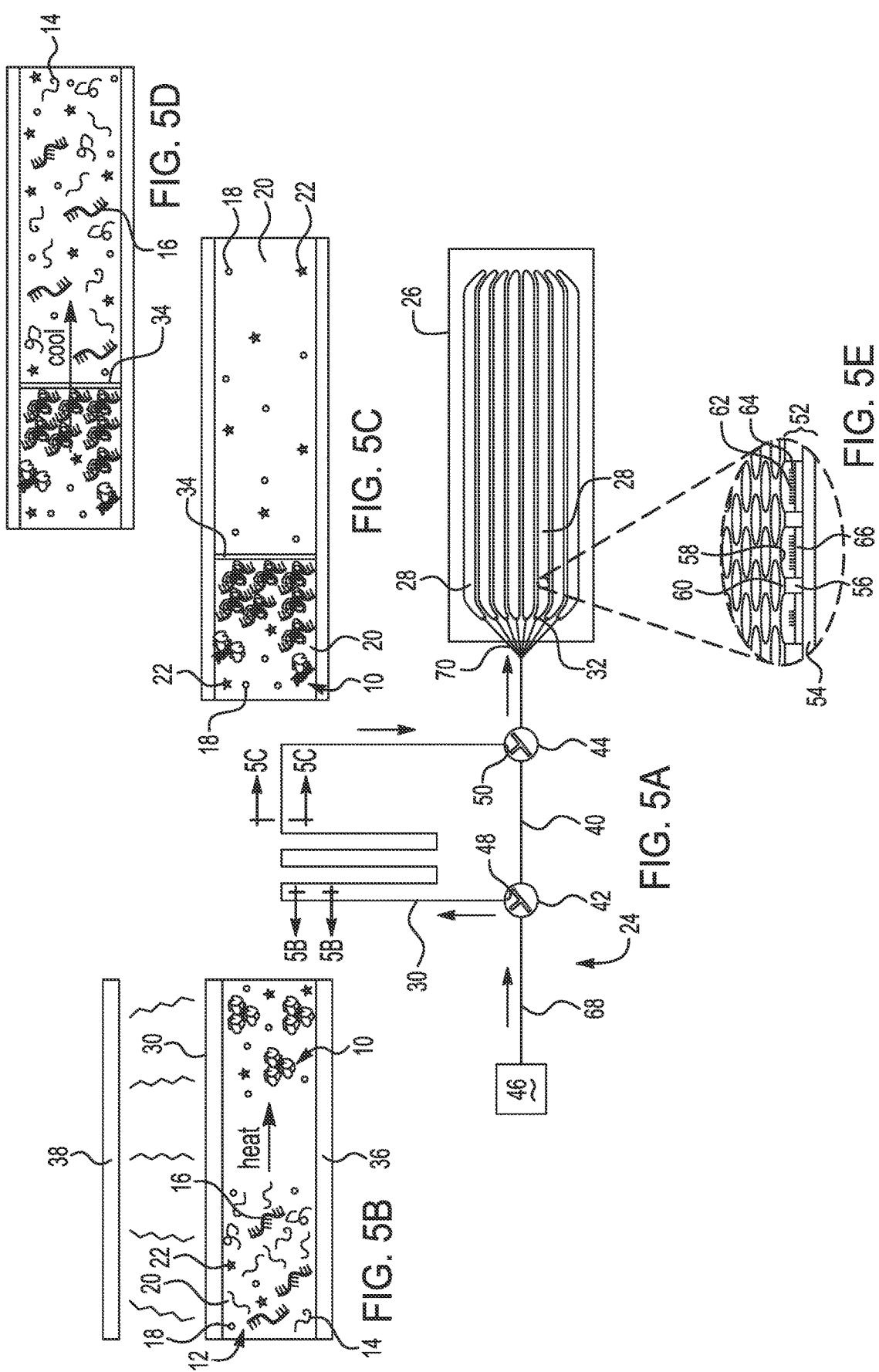
FIG. 5A is a schematic illustration of a flow cell assembly.
FIG. 5B is a cross-sectional view taken along line 5B-5B of FIG. 5A illustrating sample fluid flow in a temperature controlled flow channel and complex formation when the temperature is increased.
FIG. 5C is a cross-sectional view taken along line 5C-5C of FIG. 5A illustrating a filter in the temperature controlled flow channel and the concentration of DNA-methyl cellulose complexes at the filter.
FIG. 5D depicts the temperature controlled flow channel of FIG. 5C when the temperature is decreased.
FIG. 5E is an enlarged, perspective view of an example of a reaction chamber having a patterned sequencing surface.

FIG. 5A depicts a flow cell assembly 24 which may be used in the method 200. The flow cell assembly 24 includes a flow cell 26, which includes a reaction chamber 28 having depressions separated by interstitial regions and capture primers attached within each of the depressions (shown in FIG. 5E); a temperature controlled flow channel 30 in selective fluid communication with an inlet 32 of the reaction chamber 28; and a filter 34 (shown in FIG. 5C) positioned in the temperature controlled flow channel 30, the filter 34 i) to block concentrated deoxyribonucleic acid (DNA)-polymer complexes 10 generated in the temperature controlled flow channel 30 at a first temperature, and ii) to allow passage of concentrated DNA 16 and polymer (methyl cellulose 14) released from the complexes 10 in the temperature controlled flow channel 30 at a second temperature.

In the flow cell assembly 24, the temperature controlled flow channel 30 is positioned upstream of the flow cell 26. This positioning enables the capture and concentration of the DNA sample 16 from the sample fluid 12 before the DNA sample 16 is introduced into the reaction chamber 28 of the flow cell 26.

The temperature control flow channel 30 may be a tube, pipe, microfluidic channel, or the like. The temperature control flow channel 30 may have any shape, volume and length that is suitable for the purposes capturing and concentrating a desirable amount of the DNA sample 16 in a sample fluid 12 before it is introduced into the reaction chamber 28 of the flow cell 26. The example channel 30 shown in FIG. 5A has a serpentine shape.

The temperature controlled flow channel 30 can be heated and cooled so that a sample fluid 12 flowing through the channel 30 is also heated or cooled. In one example, the temperature controlled flow channel 30 includes an internal heating component 36 (FIG. 5B), such as a heating plate, that is positioned in the channel 30 or defines one or more interior walls of the flow channel 30. In another example, the flow cell assembly 24 includes an external heating component 38 (FIG. 5B), such as a laser, that is positioned outside of the channel 30. The external heating component 38 may be operatively positioned to direct heat toward the channel 30. Some examples of the temperature controlled flow channel 30 also include an internal cooling component (not shown), such as a thermoelectric cooler, etc., that is positioned in the channel 30 or defines one or more interior walls of the flow channel 30. Other examples of the temperature controlled flow channel 30 include an external cooling component (not shown), such as a fan, that is positioned outside of the channel 30. The internal or external component may also be a combination device that is capable of actively heating and actively cooling.

While not shown, the internal heating component 36 or the external heating component 38, and the internal cooling component or the external cooling component (when used), may be operatively connected to a temperature control unit that operates the component(s) 36 or 38, and controls the temperature of the component(s) 36 or 38. Moreover, temperature sensors may be positioned in the channel 30 to provide real-time data of the temperature in the channel 30 to the temperature control unit, so that the desired internal temperature may be obtained and/or maintained.

The flow cell assembly 24 may also include a bypass line 40 in fluid communication with an inlet 48 of the temperature controlled flow channel 30 and with an outlet 50 of the temperature controlled flow channel 30; a first bypass valve 42 to control flow of a sample fluid 12 to the inlet of the temperature controlled flow channel 30; and a second bypass valve 44 to control flow of the concentrated DNA 16 and the polymer (methyl cellulose 14) to the reaction chamber 28.

The bypass line 40 may be a tube, pipe, microfluidic channel, or the like. The bypass line 40 allows fluid(s) to be directed from a reservoir 46 or other storage unit to the reaction chamber 28 without passing through the temperature controlled flow channel 30. The bypass line 40 may be used, for example, when the fluid that is to be delivered to the reaction chamber 28 does not include the DNA sample 16, when it is not desirable to heat the fluid, or when concentration of the DNA sample 16 is not desirable. Examples of fluids that may be directed through the bypass line 40 rather than through the temperature controlled flow channel 30 include a washing fluid, a deblocking agent fluid, a reaction fluid including polymerases, sequencing primers, nucleotides, etc.

The first bypass valve 42 is switchable between two positions, one that directs the flow through the temperature controlled flow channel 30 (and thus cs the bypass line 40) and the other that directs the flow through the bypass line 40 (and thus cs the temperature controlled flow channel 30). The second bypass valve 44 is also switchable between two positions, one that directs the flow out of the temperature controlled flow channel 30 (and does not allow back flow through the bypass line 40) and the other that directs the flow through the bypass line 40 (and thus does not allow back flow through the temperature controlled flow channel 30). The arrows shown in FIG. 5A illustrate the flow of fluid when the valves 42, 44 are positioned to open the temperature controlled flow channel 30 and to c the bypass line 40. Any suitable valves may be used for the first and second bypass valves 42, 44.

The temperature controlled flow channel 30 may be connected to the inlet 32 of the reaction chamber 28 through a manifold 70 or other fluidic connector.

The temperature controlled flow channel 30 also includes the filter 34. The filter 34 may be secured within the temperature controlled flow channel 30 using an adhesive, mechanical attaching mechanism, or the like. In other examples, the filter 34 may be built into the temperature controlled flow channel 30 during manufacturing. The filter 34 may be attached to the entire interior perimeter of the temperature controlled flow channel 30. As such, the filter 34 covers the cross-sectional area (e.g., which is parallel to the inlet 48 of the temperature controlled flow channel 30).

The filter 34 in the temperature controlled flow channel 30 may have any suitable pore size that allows the aqueous carrier and any components dissolved therein to flow through, and that blocks the DNA-methyl cellulose complexes 10 from flowing through. In an example, the pore size of the filter 34 ranges from about 1 µm to about 100 µm so that unbound DNA can move through it. Examples of suitable filter materials include nitrocellulose, nylon (polyamide), etc.

In addition to the temperature controlled flow channel 30, the flow cell assembly 24 also includes the flow cell 26. One example flow cell 26 will now be described in more detail with reference to FIG. 5A and FIG. 5E.

In the example shown in FIG. 5A, the flow cell 26 includes eight reaction chambers 28. While eight reaction chambers 28 are shown, it is to be understood that any number of reaction chambers 28 may be included in the flow cell 26 (e.g., a single reaction chamber 28, four reaction chambers 28, etc.). Each reaction chamber 28 is an area defined between two bonded components (e.g., a substrate 52 and a lid or two substrates 52), which can have fluids (e.g., those described herein) introduced thereto and removed therefrom. Each reaction chamber 28 may be isolated from each other reaction chamber 28 so that fluid introduced into any particular reaction chamber 28 does not flow into any adjacent reaction chamber 28. Some examples of the fluids introduced into the reaction chamber 28 may introduce reaction components (e.g., the DNA sample 16, polymerases, sequencing primers, nucleotides, etc.), washing solutions, deblocking agents, etc.

The reaction chamber 28 is at least partially defined by a substrate 52. The substrate 52 may be a single layer structure, or may be a multi-layered structure (as shown in FIG. 5E).

Examples of suitable single layer structure materials include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HfO_2$), carbon, metals, inorganic glasses, or the like.

Some examples of the multi-layered structure include glass or silicon, with a coating layer of tantalum oxide or another ceramic oxide at the surface. Other examples of the multi-layered structure may include a silicon-on-insulator (SOI) substrate. Still other examples of the multi-layered structure, such as that shown in FIG. 5E, include an underlying support 54 (e.g., glass or silicon) having a patterned material 56 thereon. It is to be understood that any material that can be selectively deposited, or deposited and patterned to form the depressions 58 and the interstitial regions 60 may be used for the patterned material 56.

As one example of the patterned material 56, an inorganic oxide may be selectively applied to the support 52 via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example of the patterned material 56, a resin may be applied to the support 52 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane-based resin (e.g., POSS® from Hybrid Plastics), a non-polyhedral oligomeric silsesquioxane epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" refers to a chemical composition that is a hybrid intermediate (e.g., $RSiO_{1.5}$) between that of silica ($SiO_2$) and silicone ($R_2SiO$). An example of polyhedral oligomeric silsesquioxane can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for polyhedral oligomeric silsesquioxane include epoxy, azide/azido, a thiol, a poly(ethylene glycol), a norbornene, a tetrazine, acrylates, and/or methacrylates, or further, for example, alkyl, aryl, alkoxy, and/or haloalkyl groups.

In an example, the substrate 52 (single or multi-layered) may have a diameter ranging from about 2 mm to about 300 mm, or a rectangular sheet or panel having its largest dimension up to about 10 feet (~3 meters). In an example, the substrate 52 is a wafer having a diameter ranging from about 200 mm to about 300 mm. In another example, the substrate 52 is a die having a width ranging from about 0.1 mm to about 10 mm. While example dimensions have been provided, it is to be understood that a substrate 52 with any suitable dimensions may be used. For another example, a panel may be used that is a rectangular support, which has a greater surface area than a 300 mm round wafer.

In some examples, the reaction chamber 28 is etched into a glass substrate. In other examples, the reaction chamber 28 is patterned into the patterned material 56 of a multi-layered structure using photolithography, nanoimprint lithography, etc. In still other examples, a separate material (not shown) may be applied to the substrate 52 so that the separate material defines the walls of the reaction chamber 28 and the substrate 52 defines the bottom of the reaction chamber 28.

In an example, the reaction chamber 28 has a substantially rectangular configuration. The length and width of the reaction chamber 28 may be smaller, respectively, than the length and width of the substrate 52 so that a portion of the substrate surface surrounding the reaction chamber 28 is available for attachment to a lid (not shown) or another substrate 52. In some instances, the width of each reaction chamber 28 can be at least about 1 mm, at least about 2.5 mm, at least about 5 mm, at least about 7 mm, at least about 10 mm, or more. In some instances, the length of each reaction chamber 28 can be at least about 10 mm, at least about 25 mm, at least about 50 mm, at least about 100 mm, or more. The width and/or length of each reaction chamber 28 can be greater than, less than or between the values specified above. In another example, the reaction chamber 28 is square (e.g., 10 mm×10 mm).

The depth of the reaction chamber 28 can be as small as a monolayer thick when microcontact, aerosol, or inkjet printing is used to deposit a separate material that defines the reaction chamber 28 walls. For other examples, the depth of the reaction chamber 28 can be about 1 µm, about 10 µm, about 50 µm, about 100 µm, or more. In an example, the depth may range from about 10 µm to about 100 µm. In another example, the depth may range from about 10 µm to about 30 µm. In still another example, the depth is about 5 µm or less. It is to be understood that the depth of the reaction chamber 28 may be greater than, less than or between the values specified above.

Each reaction chamber 28 is in fluid communication with an inlet and an outlet (not shown). The inlet and outlet of each reaction chamber 28 may be positioned at opposed ends of the flow cell 26. The inlets and outlets of the respective reaction chambers 28 may alternatively be positioned anywhere along the length and width of the reaction chamber 28 that enables desirable fluid flow.

The inlet allows fluids to be introduced into the reaction chamber 28, and the outlet allows fluid to be extracted from the reaction chamber 28. Each of the inlets and outlets is fluidly connected to a fluidic control system (including, e.g., reservoirs 46, pumps, valves 42, 44, waste containers, and the like) which controls fluid introduction and expulsion.

FIG. 5E depicts an example of the architecture within the reaction chamber 28. The architecture includes depressions 58 separated by interstitial regions 60. The depressions 58 may be defined in the substrate 52. In one example, the depressions 58 are defined in a single layer structure (e.g., etched into glass), or, as shown in FIG. 5E, in the patterned material 56 of the multi-layered structure.

Many different layouts of the depressions 58 may be envisaged, including regular, repeating, and non-regular patterns. In an example, the depressions 58 are disposed in a hexagonal grid for c packing and improved density. Other layouts may include, for example, rectilinear (rectangular) layouts, triangular layouts, and so forth. In some examples, the layout or pattern can be an x-y format of depressions 58 that are in rows and columns. In some other examples, the layout or pattern can be a repeating arrangement of depressions 58 and/or interstitial regions 60. In still other examples, the layout or pattern can be a random arrangement of depressions 58 and/or interstitial regions 60.

The layout or pattern of the depressions 58 may be characterized with respect to the density of the depressions 58 (number of depressions 58) in a defined area. For example, the depressions 58 may be present at a density of approximately 2 million per mm². The density may be tuned to different densities including, for example, a density of about 100 per mm², about 1,000 per mm², about 0.1 million per mm², about 1 million per mm², about 2 million per mm², about 5 million per mm², about 10 million per mm², about 50 million per mm², or more, or less. It is to be further understood that the density of depressions 58 in the patterned material 56 can be between one of the lower values and one of the upper values selected from the ranges above. As examples, a high density array may be characterized as having depressions 58 separated by less than about 100 nm, a medium density array may be characterized as having depressions 58 separated by about 400 nm to about 1 µm, and a low density array may be characterized as having depressions 58 separated by greater than about 1 µm. While example densities have been provided, it is to be understood that any suitable densities may be used. The density of the depressions 58 may depend, in part, on the depth of the depressions 58. In some instances, it may be desirable for the spacing between depressions 58 to be even greater than the examples listed herein.

The layout or pattern of the depressions 58 may also or alternatively be characterized in terms of the average pitch, or the spacing from the center of the depression 58 to the center of an adjacent depression 58 (center-to-center spacing) or from the right edge of one depression 58 to the left edge of an adjacent depression 58 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 58 can be between one of the lower values and one of the upper values selected from the ranges above. In an example, the depressions 58 have a pitch (center-to-center spacing) of about 1.5 µm. While example average pitch values have been provided, it is to be understood that other average pitch values may be used.

The size of each depression 58 may be characterized by its volume, opening area, depth, and/or diameter.

Each depression 58 can have any volume that is capable of confining a fluid. The minimum or maximum volume can be selected, for example, to accommodate the throughput (e.g., multiplexity), resolution, nucleotides, or analyte reactivity expected for downstream uses of the flow cell 26. For example, the volume can be at least about $1\times10^{-3}$ µm³, at least about $1\times10^{-2}$ µm³, at least about 0.1 µm³, at least about 1 µm³, at least about 10 µm³, at least about 100 µm³, or more. Alternatively or additionally, the volume can be at most about $1\times10^{4}$ µm³, at most about $1\times10^{3}$ µm³, at most about 100 µm³, at most about 10 µm³, at most about 1 µm³, at most about 0.1 µm³, or less.

The area occupied by each depression opening can be selected based upon similar criteria as those set forth above for the volume. For example, the area for each depression opening can be at least about $1-10^{-3}$ µm², at least about $1\times10^{-2}$ µm², at least about 0.1 µm², at least about 1 µm², at least about 10 µm², at least about 100 µm², or more. Alternatively or additionally, the area can be at most about $1\times10^{3}$ µm², at most about 100 µm², at most about 10 µm², at most about 1 µm², at most about 0.1 µm², at most about $1\times10^{-2}$ µm², or less. The area occupied by each depression opening can be greater than, less than or between the values specified above.

The depth of each depression 58 can large enough to house a polymeric hydrogel 66 and capture primers 62, 64. In an example, the depth may be at least about 0.1 µm, at least about 0.5 µm, at least about 1 µm, at least about 10 µm, at least about 100 µm, or more. Alternatively or additionally, the depth can be at most about $1\times10^{3}$ µm, at most about 100 µm, at most about 10 µm, or less. In some examples, the depth is about 0.4 µm. The depth of each depression 58 can be greater than, less than or between the values specified above.

In some instances, the diameter or length and width of each depression 58 can be at least about 50 nm, at least about 0.1 µm, at least about 0.5 µm, at least about 1 µm, at least about 10 µm, at least about 100 µm, or more. Alternatively or additionally, the diameter or length and width can be at most about $1\times10^{3}$ µm, at most about 100 µm, at most about 10 µm, at most about 1 µm, at most about 0.5 µm, at most about 0.1 µm, or less (e.g., about 50 nm). In some examples, the diameter or length and width is about 0.4 µm. The diameter or length and width of each depression 58 can be greater than, less than or between the values specified above.

A polymeric hydrogel 66 is present in each of the depressions 58. An example of the polymeric hydrogel 66 includes an acrylamide copolymer represented by the following structure (I):

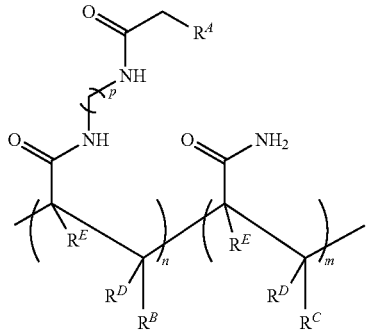

wherein:

$R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;

$R^B$ is H or optionally substituted alkyl;

$R^C$, $R^D$, and $R^E$ are each independently selected from the group consisting of H and optionally substituted alkyl;

each of the $-(CH_2)_p-$ can be optionally substituted;

p is an integer in the range of 1 to 50;

n is an integer in the range of 1 to 50,000; and m is an integer in the range of 1 to 100,000.

One specific example of the acrylamide copolymer represented by structure (I) is poly(N-(5-azidoacetamidylpentyl)acrylamide-co-acrylamide (PAZAM).

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of PAZAM and other forms of the acrylamide copolymer may range from about 5 kDa to about 1500 kDa or from about 10 kDa to about 1000 kDa, or may be, in a specific example, about 312 kDa.

In some examples, PAZAM and other forms of the acrylamide copolymer are linear polymers. In some other examples, PAZAM and other forms of the acrylamide copolymer are lightly cross-linked polymers.

In other examples, the polymeric hydrogel 66 may be a variation of the structure (I). In one example, the acrylamide unit may be replaced with N,N-dimethylacrylamide

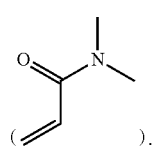

In this example, the acrylamide unit in structure (I) may be replaced with

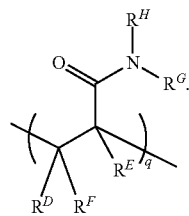

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

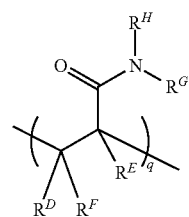

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

As another example of the polymeric hydrogel 66, the recurring "n" feature in structure (I) may be replaced with a monomer including a heterocyclic azido group having structure (II):

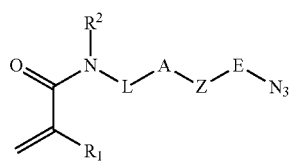

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 ring members present as a single cyclic structure or a fused structure. Some specific examples of Z include pyrrolidinyl, pyridinyl, or pyrimidinyl.

As still another example, the polymeric hydrogel 66 may include a recurring unit of each of structure (III) and (IV):

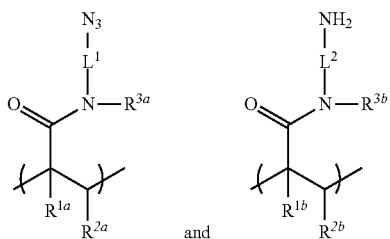

wherein each of $R^{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

It is to be understood that other molecules may be used to form the polymeric hydrogel 66, as long as they are functionalized to graft oligonucleotide primers 62, 64 thereto. Other examples of suitable polymer layers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymeric hydrogels 66 include mixed copolymers of acrylam ides and acrylates. A variety of polymer architectures containing acrylic monomers (e.g., acrylamides, acrylates etc.) may be utilized in the examples disclosed herein, such as branched polymers, including star polymers, star-shaped or star-block polymers, dendrimers, and the like. For example, the monomers (e.g., acrylamide, acrylamide containing the catalyst, etc.) may be incorporated, either randomly or in block, into the branches (arms) of a star-shaped polymer.

In still another example, the acrylamide copolymer is formed using nitroxide mediated polymerization, and thus at least some of the copolymer chains have an alkoxyamine end group. In the copolymer chain, the term "alkoxyamine end group" refers to the dormant species —$ONR_1R_2$, where each of $R_1$ and $R_2$ may be the same or different, and may independently be a linear or branched alkyl, or a ring structure, and where the oxygen atom is attached to the rest of the copolymer chain. In some examples, the alkoxyamine may also be introduced into some of the recurring acrylamide monomers, e.g., at position $R^4$ in structure (I). As such, in one example, structure (I) includes an alkoxyamine end group; and in another example, structure (I) includes an alkoxyamine end group and alkoxyamine groups in at least some of the side chains.

In the example shown in FIG. 5E, the polymeric hydrogel 66 is positioned within each of the depressions 58, and not on the surrounding interstitial regions 60.

To introduce the polymeric hydrogel 66 into the depressions 58, a mixture of the polymeric hydrogel 66 may be generated and then applied to the substrate 52. In one example, the polymeric hydrogel 66 may be present in a mixture (e.g., with water or with ethanol and water). The mixture may then be applied to the substrate surfaces (including in the depressions 58) using spin coating, or dipping or dip coating, spray coating, or flow of the material under positive or negative pressure, or another suitable technique. These types of techniques blanketly deposit the polymeric hydrogel 66 on the patterned material 56 (e.g., in the depressions 58 and on interstitial regions 60. Other selective deposition techniques (e.g., involving a mask, controlled printing techniques, etc.) may be used to specifically deposit the polymeric hydrogel 66 in the depressions 58 and not on the interstitial regions 60.

In some examples, the substrate surface may be activated, and then the mixture (including the polymeric hydrogel 66) may be applied thereto. In one example, a silane or silane derivative (e.g., norbornene silane) may be deposited on the substrate surface using vapor deposition, spin coating, or other deposition methods. In another example, the substrate surface may be exposed to plasma ashing to generate surface-activating agent(s) (e.g., —OH groups) that can adhere to the polymeric hydrogel 66.

Depending upon the polymeric hydrogel 66, the applied mixture may be exposed to a curing process. In an example, curing may take place at a temperature ranging from room temperature (e.g., about 25° C.) to about 95° C. for a time ranging from about 1 millisecond to about several days.

In some examples, polishing may then be performed in order to remove the polymeric hydrogel 66 from the interstitial regions 60, while leaving the polymeric hydrogel 66 in the depressions 58 at least substantially intact.

The flow cell 26 also includes capture primers 62, 64.

A grafting process may be performed to graft the capture primers 62, 64 to the polymeric hydrogel 66 in the depressions 58. In an example, the capture primers 62, 64 can be immobilized to the polymeric hydrogel 66 by single point covalent attachment at or near the 5' end of the primers 62, 64. This attachment leaves i) an adapter-specific portion of the primers 62, 64 free to anneal to its cognate nucleic acid fragment and ii) the 3' hydroxyl group free for primer extension. Any suitable covalent attachment may be used for this purpose. Examples of terminated primers that may be used include alkyne terminated primers, which can attach to an azide moiety of the polymeric hydrogel 66. Specific examples of suitable primers 62, 64 include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms.

In an example, grafting may involve flow through deposition (e.g., using a temporarily bound or permanently bonded lid), dunk coating, spray coating, puddle dispensing, or by another suitable method that will attach the primer(s) 62, 64 to the polymeric hydrogel 66 in the depressions 58. Each of these example techniques may utilize a primer solution or mixture, which may include the primer(s) 62, 64, water, a buffer, and a catalyst. With any of the grafting methods, the primers 62, 64 react with reactive groups of polymeric hydrogel 66 and have no affinity for the surrounding interstitial regions 60. As such, the primers 62, 64 selectively graft to the polymeric hydrogel 66 and not on the interstitial regions 60.

While not shown in FIG. 5A or 5E, it is to be understood that the flow cell 26 may also include a lid attached to the substrate 52. In an example, the lid may be bonded to at least a portion of the substrate 52, e.g., at some of the interstitial regions 60. In one example, the lid is bonded at a perimeter and between the reaction chambers 28. The bond that is formed between the lid and the substrate 52 may be a chemical bond, or a mechanical bond (e.g., using a fastener, etc.).

The lid may be any material that is transparent to an excitation light that is directed toward the substrate 52. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid may be bonded to the substrate 52 using any suitable technique, such as laser bonding, diffusion bonding, anodic bonding, eutectic bonding, plasma activation bonding, glass frit bonding, or others methods known in the art. In an example, a spacer layer may be used to bond the lid to the substrate 52. The spacer layer may be any material that will seal at least some of the substrate 52 and the lid together. In some examples, the spacer layer can be a radiation-absorbing material that aids in bonding of the substrate 52 and the lid.

In other examples, instead of a lid, the flow cell 26 may include two substrates 52 bonded together so that the reaction chambers 28 face each other and a fluid channel is defined therebetween. The two substrates 52 may be bonded together at some of the interstitial regions 60 (e.g., at a perimeter and between the reaction chambers 28). The bond that is formed between the substrates 52 may be a chemical bond, or a mechanical bond (e.g., using a fastener, etc.).

Referring back to the method 200, the sample fluid 12 (shown in FIG. 5B) is introduced to the temperature controlled flow channel 30. The sample fluid 12 may be stored in or introduced into the reservoir 46 and then pumped through an introduction line 68 that is fluidly connected to the first bypass valve 42, the bypass line 40, and the temperature controlled flow channel 30. The first bypass valve 42 may be positioned so that the sample fluid 12 is directed to the temperature controlled flow channel 30.

When the sample fluid 12 is introduced into the temperature controlled flow channel 30, the temperature of the flow channel 30 and the sample fluid 12 are below the gelation temperature of the methyl cellulose 14 in the sample fluid 12. At this temperature, the methyl cellulose 14, the chemically inert polymer 18, and the salt 22 are dissolved in the aqueous carrier 20, while the DNA sample 16 is dispersed in the aqueous carrier 20. This is shown schematically at the left side of the temperature controlled flow channel 30 in FIG. 5B.

The method 200 also involves heating the temperature controlled flow channel 30 as the sample fluid 12 is introduced thereto. The temperature to which the temperature controlled flow channel 30 is heated will depend upon the gelation temperature of the methyl cellulose 14 in the sample fluid 12. The temperature controlled flow channel 30 may be brought to the gelation temperature or above the gelation temperature so that the temperature of the sample fluid 12 is able to reach the gelation temperature.

The internal or external heating component 36 or 38 may be used to heat the temperature controlled flow channel 30. Sensor feedback may be used to achieve and/or maintain the desired temperature.

As shown at the right side of the temperature controlled flow channel 30 in in FIG. 5B, the heat causes the methyl cellulose 14 to precipitate out of the aqueous carrier 20. The precipitated methyl cellulose polymer chains physically interact with the DNA sample 16 to form DNA-methyl cellulose complexes 10 within the temperature controlled flow channel 30.

The method 200 also involves continuing the flow of the sample fluid 12 through the temperature controlled flow channel 30 as the temperature controlled flow channel is heated. This causes the DNA-methyl cellulose complexes 10 to flow toward the filter 34, where they are blocked from flowing further. This concentrates a plurality of the DNA-methyl cellulose complexes 10 at the filter 34 in the temperature controlled flow channel 30, as shown in FIG. 5C.

It is to be understood that the aqueous carrier 20 and any components dissolved therein, such as the salt 22 and the chemically inert polymer 18, may continue to flow through the filter 34 even though the DNA-methyl cellulose complexes 10 are blocked. The aqueous carrier 20 and any components dissolved therein may be directed directly to a waste receptacle (not shown), or may be directed to and through the flow cell 26 into the waste receptacle.

The method 200 further includes cooling the temperature controlled flow channel 30 such that a temperature of the sample fluid 12 contained therein is decreased to below the gelation temperature of the methyl cellulose 14. In some examples, the internal or external heating component 36 or 38 may be turned off to cool the temperature controlled flow channel 30. This involves passive cooling as the sample fluid is allowed to cool on its own. In other examples, the temperature controlled flow channel 30 may include a cooling component or a heating/cooling component that can be controlled to actively reduce the temperature of the temperature controlled flow channel 30 and the sample fluid 12 contained therein.

Cooling may be initiated after a predetermined duration of sample fluid 12 flow, and/or when a desired amount of the sample fluid 12 has been introduced to the temperature controlled flow channel 30, and/or when a desired number of complexes 10 have been concentrated at the filter 34. As examples, the volume of fluid passing the filter 34 may be calculated, or a particular counter may be incorporated in line at the filter 34.

The temperature to which the temperature controlled flow channel 30 is cooled will depend upon the gelation temperature of the methyl cellulose 14 in the sample fluid 12. The temperature controlled flow channel 30 may be reduced below the gelation temperature so that the temperature of the sample fluid 12 is also able to cool to below the gelation temperature.

As shown in FIG. 5D, cooling detangles the DNA-methyl cellulose complexes 10 in the temperature controlled flow channel 30, e.g., concentrated at the filter 34. More specifically, cooling causes the methyl cellulose 14 to dissolve in the aqueous carrier 20, which detangles the DNA-methyl cellulose complexes 10 and releases the DNA sample 16. The dissolved methyl cellulose 14 and the DNA sample 16 are both able to flow through the filter 34 and out of the temperature controlled flow channel 30.

The method 200 may further include transporting the DNA sample 16 and the methyl cellulose 14 to the flow cell 26 and into the reaction chamber(s) 28 for analysis (e.g., sequencing).

The flow cell assembly 24 described in connection with the method 200 may be part of a kit, which may also include an example of the sample fluid 12.

DNA Seeding

Figure 6:
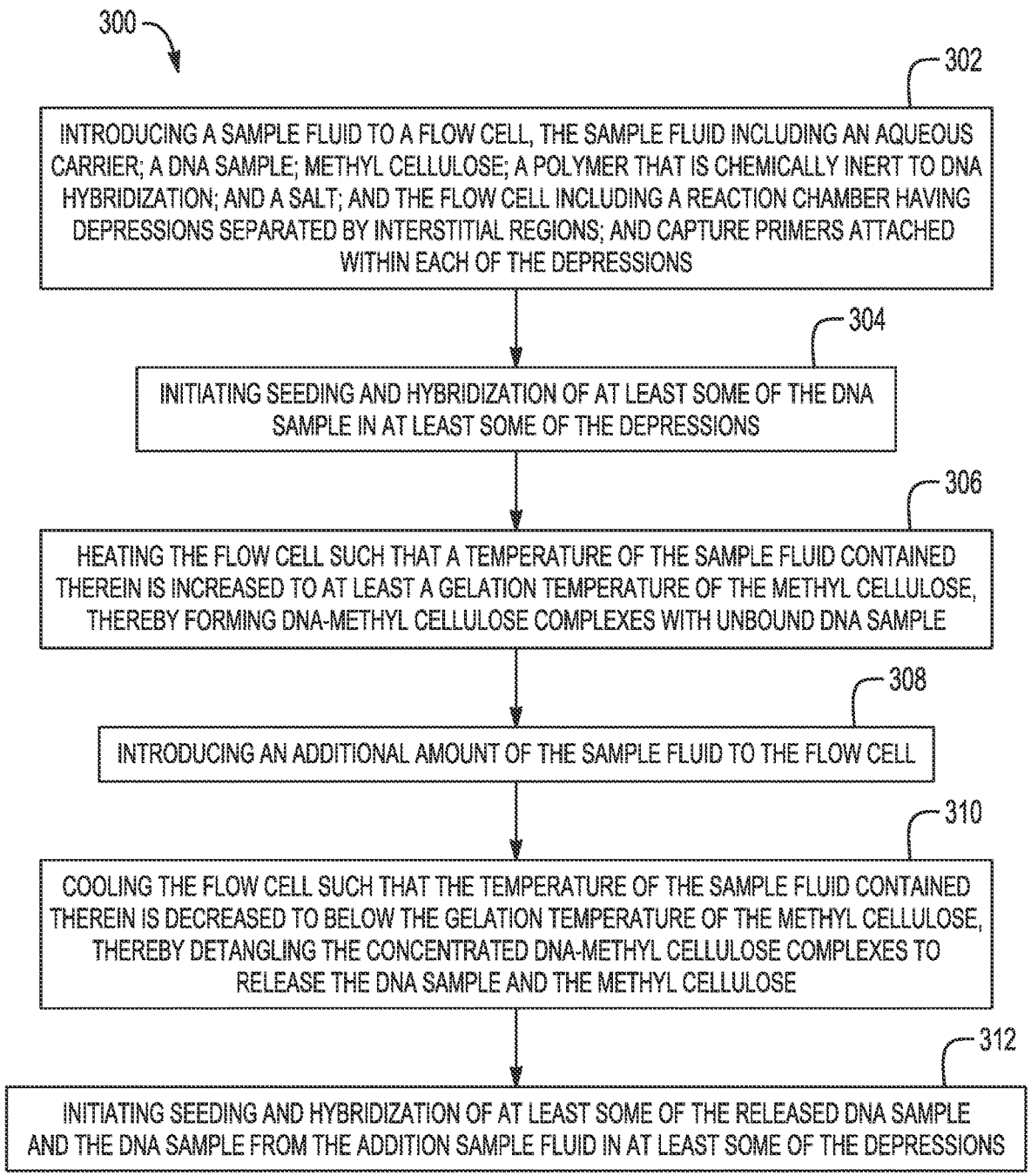
FIG. 6 is a flow diagram illustrating an example of a method for improving DNA seeding on a flow cell surface.

Another example method is shown at reference numeral 300 in FIG. 6. This example method 300 may be used to improve DNA seeding for sequencing. The method 300 includes introducing a sample fluid to a flow cell, the sample fluid including an aqueous carrier, a DNA sample, methyl cellulose, a polymer that is chemically inert to DNA hybridization, and a salt; and the flow cell including a reaction chamber having depressions separated by interstitial regions, and capture primers attached within each of the depressions (reference numeral 302); initiating seeding and hybridization of at least some of the DNA sample in at least some of the depressions (reference numeral 304); heating the flow cell such that a temperature of the sample fluid contained therein is increased to at least a gelation temperature of the methyl cellulose, thereby forming DNA-methyl cellulose complexes with unbound DNA sample (reference numeral 306); introducing an additional amount of the sample fluid to the flow cell (reference numeral 308); cooling the flow cell such that the temperature of the sample fluid contained therein is decreased to below the gelation temperature of the methyl cellulose, thereby detangling the concentrated DNA-methyl cellulose complexes to release the DNA sample and the methyl cellulose (reference numeral 310); and initiating seeding and hybridization of at least some of the released DNA sample and the DNA sample from the additional sample fluid in at least some of the depressions (reference numeral 312).

The method 300 is shown schematically in FIG. 7A through 7F.

In this example of the method 300, the DNA sample 16 in the sample fluid 12 includes DNA library fragments. The DNA library fragments include adapters at opposed ends. The DNA library fragments may be prepared using any library preparation technique that fragments a longer piece of genetic material and incorporates the desired adapters to the ends of the fragments. Some example library preparation techniques include tagmentation or ligation.

Figure 7:
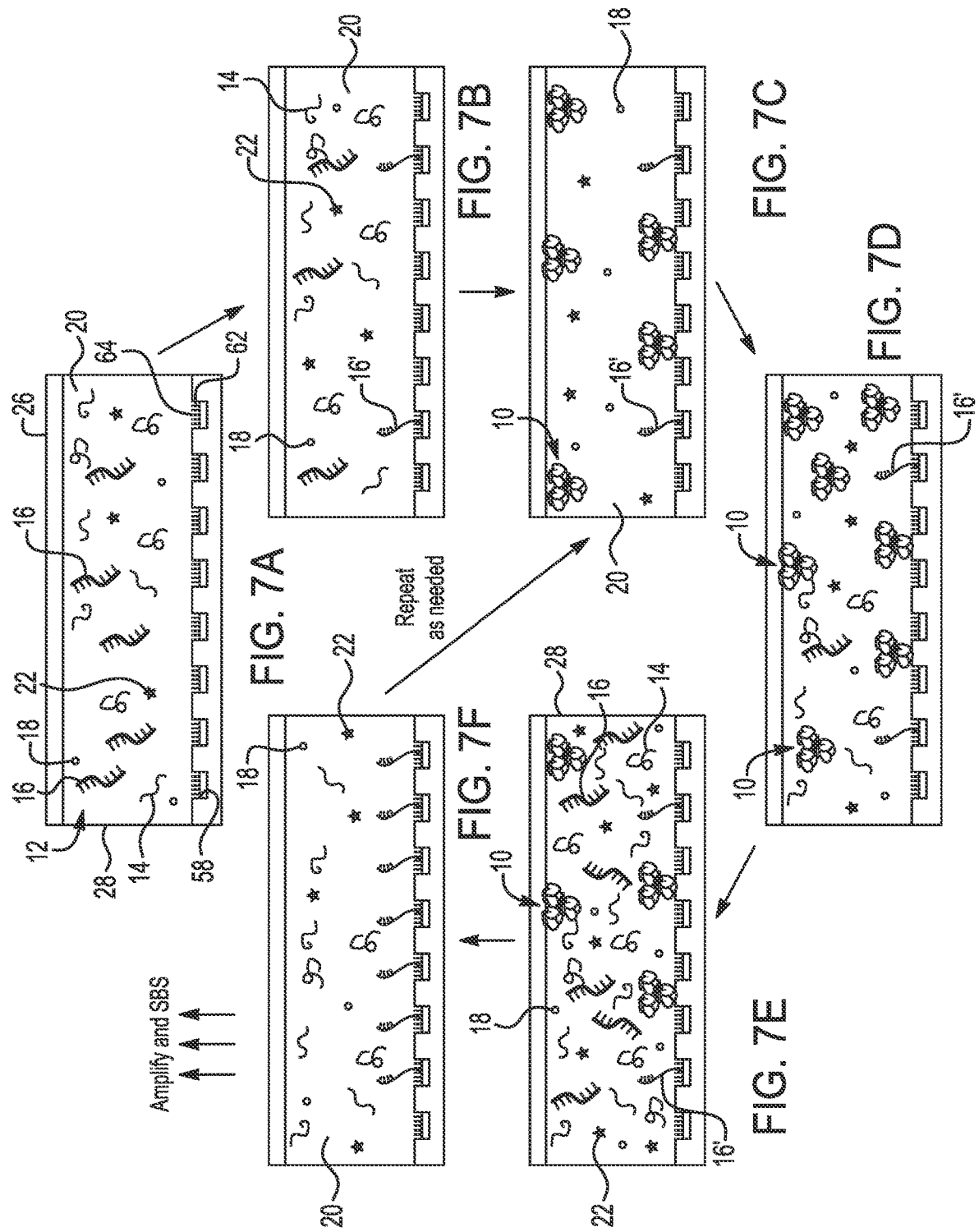
FIGS. 7A through 7F schematically illustrate the method of FIG. 6.

In FIG. 7A, the sample fluid 12 is introduced to the flow cell 26. More specifically, the sample fluid 12 is introduced into the reaction chamber 28, which includes depressions 58 separated by interstitial regions 60 and capture primers 62, 64 attached within the depressions 58.

When the sample fluid 12 is introduced into the reaction chamber 28, seeding (e.g., immobilization) of the DNA sample 16 may be initiated, as shown at FIG. 7B. Seeding is accomplished through hybridization between one of the adapters on the DNA sample 16 and a complementary one of the capture primers 62, 64. Seeding may be performed at a suitable hybridization temperature for the DNA sample 16 and the capture primers 62, 64. The DNA sample 16 that has been seeded is shown at reference numeral 16' and is referred to herein as the seeded DNA library fragments 16'.

The method 300 then involves heating the flow cell 26. The temperature to which the flow cell 26 is heated will depend upon the gelation temperature of the methyl cellulose 14 in the sample fluid 12. The flow cell 26 may be brought to the gelation temperature or above the gelation temperature so that the temperature of the sample fluid 12 is able to reach the gelation temperature.

Throughout the method 300, heating and cooling of the flow cell 26, for example, to a suitable hybridization temperature, at, above, or below the gelation temperature, etc. may involve an internal or external heating component, similar to the components 36 or 38 described herein. An internal heating component may be positioned within the reaction chamber 28, or an external heating component may be part of a sequencing device into which the flow cell 26 is placed. The internal or external heating component may be controlled to heat the flow cell 26, or a specific reaction chamber 28 thereof, to the desired temperature. Sensor feedback may be used to achieve and/or maintain the desired temperature.

As shown in FIG. 7C, the heat causes the methyl cellulose 14 to precipitate out of the aqueous carrier 20, and the precipitated methyl cellulose polymer chains physically interact with unbound DNA sample 16 (e.g., non-seeded DNA library fragments) to form DNA-methyl cellulose complexes 10 within the reaction chamber 28. Any of the DNA sample 16 that has not been seeded/immobilized may become entangled in the DNA-methyl cellulose complexes 10. The seeded DNA library fragments 16' are hydrogen bonded to respective capture primers 62, 64, and thus do not become entangled in the complexes 10.

The method 300 also involves introducing an additional amount of the sample fluid 12 into the reaction chamber 28 of the flow cell 26. This introduction occurs as the flow cell 26 is heated. This introduction may occur relatively rapidly, so that complexation takes place within the reaction chamber 28 and not within fluidic lines leading to the reaction chamber 28. Furthermore, the rapid introduction of the additional sample fluid 12 may help to balance DNA complexation with DNA hybridization. The introduction of the additional sample fluid may take place within a few minutes, e.g., 5 minutes or less. The newly introduced methyl cellulose 14 precipitates due to the heat, and complexes with the unbound DNA sample 16 to form additional DNA-methyl cellulose complexes 10. This concentrates a plurality of the DNA-methyl cellulose complexes 10 in the reaction chamber 28, as shown in FIG. 5D.

The method 300 further includes cooling the flow cell 26 (or a reaction chamber 28 thereof) such that a temperature of the sample fluid 12 contained therein is decreased to below the gelation temperature of the methyl cellulose 14. The internal or external heating component may be turned off to cool the flow cell 26 or reaction chamber 28. This involves passive cooling as the sample fluid 12 is allowed to cool on its own. In other examples, the flow cell 26 may include a cooling component or a heating/cooling component that can be controlled to actively reduce the temperature of the reaction chamber 28 and the sample fluid 12 contained therein.

Cooling may be initiated when a desired amount of the sample fluid 12 has been introduced to the reaction chamber 28 and/or when a desired number of complexes 10 have been concentrated in the reaction chamber 28.

The temperature to which the flow cell 26 (or a reaction chamber 28 thereof) is cooled will depend upon the gelation temperature of the methyl cellulose 14 in the sample fluid 12. The flow cell 26 (or a reaction chamber 28 thereof) may be reduced below the gelation temperature so that the temperature of the sample fluid 12 is also able to cool to below the gelation temperature.

As shown in FIG. 7E, cooling detangles the DNA-methyl cellulose complexes 10 in the reaction chamber 28. More specifically, cooling causes the methyl cellulose 14 to dissolve in the aqueous carrier 20, which detangles the DNA-methyl cellulose complexes 10 and releases the DNA sample 16. The DNA sample 16 is thus concentrated in the reaction chamber 28.

When the DNA sample 16 is released from the complexes 10, seeding (e.g., immobilization) of the DNA sample 16 may again be initiated, as shown at FIG. 7F. With a higher concentration of the DNA sample 16 in the reaction chamber 28, seeding may be more effective in that a higher number of DNA library fragments (sample 16) become immobilized in the depressions 58 compared, for example, to the seeding event that occurs in FIG. 7B. As mentioned herein, seeding may be performed at a suitable hybridization temperature for the DNA sample 16 and the capture primers 62, 64.

The method 300 may further include introducing a washing solution to remove any remaining unbound DNA sample 16 (e.g., non-seeded DNA library fragments) as well as the sample fluid 12; and then initiating a sequencing cycle. The following example describes a sequencing by synthesis (SBS) cycle.

The SBS cycle may begin with amplification of the seeded DNA library fragments 16' using cluster generation. In one example of cluster generation, the seeded DNA library fragments 16' are copied from the hybridized primers 62, 64 by 3' extension using a high-fidelity DNA polymerase. The original seeded DNA library fragments 16' are denatured, leaving the copies immobilized to the capture primers 62, 64. Isothermal bridge amplification or some other form of amplification may be used to amplify the immobilized copies. For example, the copied templates loop over to hybridize to an adjacent, complementary primer 62, 64, and a polymerase copies the copied templates to form double stranded bridges, which are denatured to form two single stranded strands. These two strands loop over and hybridize to adjacent, complementary primers 62, 64, and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. Clustering results in the formation of several template polynucleotide strands along the reaction chamber 28. This example of clustering is bridge amplification, and is one example of the amplification that may be performed. It is to be understood that other amplification techniques may be used, such as the exclusion amplification (Examp) workflow (Illumina Inc.).

A sequencing primer may be introduced that hybridizes to a complementary sequence on the template polynucleotide strand. This sequencing primer renders the template polynucleotide strand ready for sequencing. The 3'-ends of the templates and any flow cell-bound primers 62, 64 (not attached to the copy) may be blocked to prevent interference with the sequencing reaction, and in particular, to prevent undesirable priming.

To initiate sequencing, an incorporation mix may be added to the flow cell 26. In one example, the incorporation mix includes a liquid carrier, a polymerase, and fluorescently labeled nucleotides. The fluorescently labeled nucleotides may include a 3' OH blocking group. When the incorporation mix is introduced into the flow cell 26, the fluid enters the reaction chamber 28, and in some examples, into the depressions 58 (where the template polynucleotide strands are present).

The fluorescently labeled nucleotides are added to the sequencing primer (thereby extending the sequencing primer) in a template dependent fashion such that detection of the order and type of nucleotides added to the sequencing primer can be used to determine the sequence of the template. More particularly, one of the nucleotides is incorporated, by a respective polymerase, into a nascent strand that extends the sequencing primer and that is complementary to the template polynucleotide strand. In other words, in at least some of the template polynucleotide strands across the flow cell 26, respective polymerases extend the hybridized sequencing primer by one of the nucleotides in the incorporation mix.

The incorporation of the nucleotides can be detected through an imaging event. During an imaging event, an illumination system (not shown) may provide an excitation light to the reaction chamber 28.

In some examples, the nucleotides can further include a reversible termination property (e.g., the 3' OH blocking group) that terminates further primer extension once a nucleotide has been added to the sequencing primer. For example, a nucleotide analog having a reversible terminator moiety can be added to the sequencing primer such that subsequent extension cannot occur until a deblocking agent is delivered to remove the moiety. Thus, for examples that use reversible termination, a deblocking reagent can be delivered to the flow cell 26 after detection occurs.

A wash or washes may take place between the various fluid delivery steps. The SBS cycle can then be repeated n times to extend the sequencing primer by n nucleotides, thereby detecting a sequence of length n.

In some examples, the forward strands may be sequenced and removed, and then reverse strands are constructed and sequenced as described herein.

While SBS has been described in detail, it is to be understood that the flow cells 26 described herein may be utilized with other sequencing protocol, for genotyping, or in other chemical and/or biological applications. In some instances, the primers 62, 64 of the flow cell 26 may be selected to enable simultaneous paired-end sequencing, where both forward and reverse strands are present on the polymeric hydrogel 66 allowing for simultaneous base calling of each read. Sequential and simultaneously paired-end sequencing facilitates detection of genomic rearrangements and repetitive sequence elements, as well as gene fusions and novel transcripts.

To further illustrate the present disclosure, examples are given herein. It is to be understood that these examples are provided for illustrative purposes and are not to be construed as limiting the scope of the present disclosure.

EXAMPLES

Example 1

Several sample fluids were prepared to examine the effect of salt on the gelation/precipitation temperature of the methyl cellulose. Each solution included 1 wt % methyl cellulose (METHOCEL® E from Dow Chemical Co.), 16 wt % polyethylene glycol (weight average molecular weight 1000 g/mol), different concentrations of sodium chloride (NaCl), and water. The concentrations of NaCl ranged from 0.4 M to 2 M.

Figure 8:
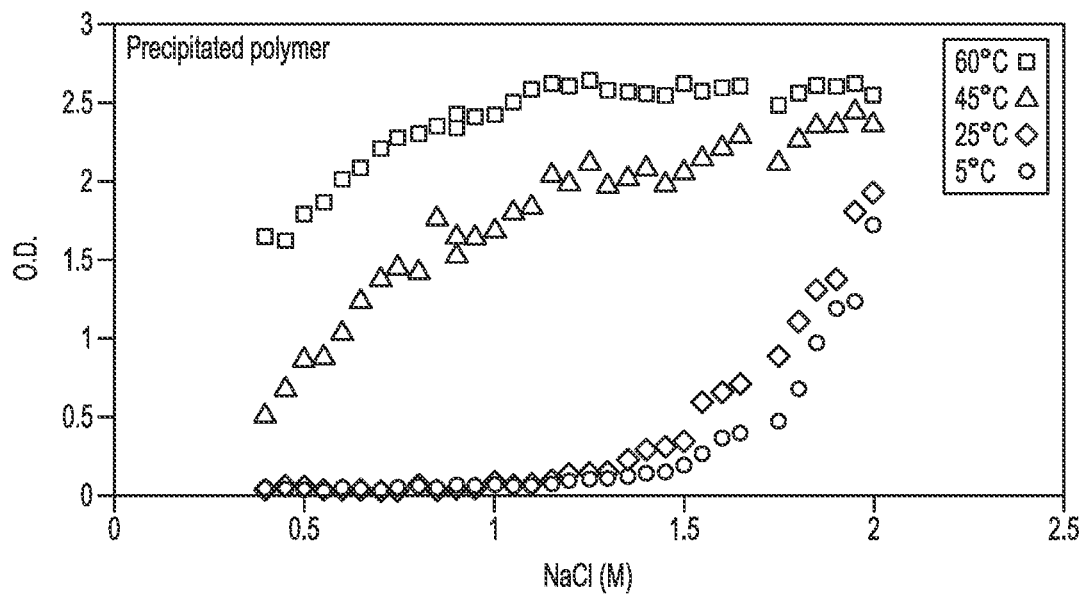
FIG. 8 is a graph depicting the turbidity (Y-axis, optical density) versus the salt concentration (X-axis, M) in aqueous solutions including 1 wt % methyl cellulose and 16 wt % polyethylene glycol when exposed to different temperatures.

Different solutions were exposed to different temperatures (5° C., 25° C., 45° C., or 60° C.) in an effort to achieve methyl cellulose precipitation. The optical density of each solution was measured using a plate reader. Optical density is a measure of light scatter, and a higher number is indicative of more precipitated methyl cellulose. An optical density of less than 0.1 meant that all of the methyl cellulose was in solution. The results are shown in FIG. 8. At the lower temperatures (5° C. and 25° C.) and lower salt concentrations (1.25 M or less), the methyl cellulose was fully dissolved. As the salt concentration was increased, the methyl cellulose was able to precipitate out of solution at the lower temperatures. These results demonstrate that the salt concentration in the sample fluids disclosed herein may be used to adjust the gelation/precipitation temperature so that the complexes disclosed herein can be generated at a desirable temperature.

Example 2

A sample fluid was prepared with a DNA ladder, which included a plurality of differently sized DNA inserts. The sample fluid included water, methyl cellulose (1% METHOCEL® E from Dow Chemical Co.), polyethylene glycol (5%, weight average molecular weight 1000 g/mol)), and 1 M NaCl. The DNA inserts were added to the solution to form the sample fluid. The sample fluid was then incubated for 5 minutes with heat at 25° C. The sample fluid was then centrifuged and decanted. The first supernatant was collected and run on an Agilent TapeStation.

The precipitate was rinsed to remove unbound DNA and was re-suspended in a saline sodium citrate buffer. The reconstituted sample fluid was again heated, this time at 60° C. for 5 minutes. The reconstituted sample fluid was then centrifuged and decanted. The second supernatant was collected and removed, leaving the precipitate solids. The precipitate solids were suspended in buffer and cooled (to release any bound DNA inserts). This solution was run on the TapeStation.

Figure 9:
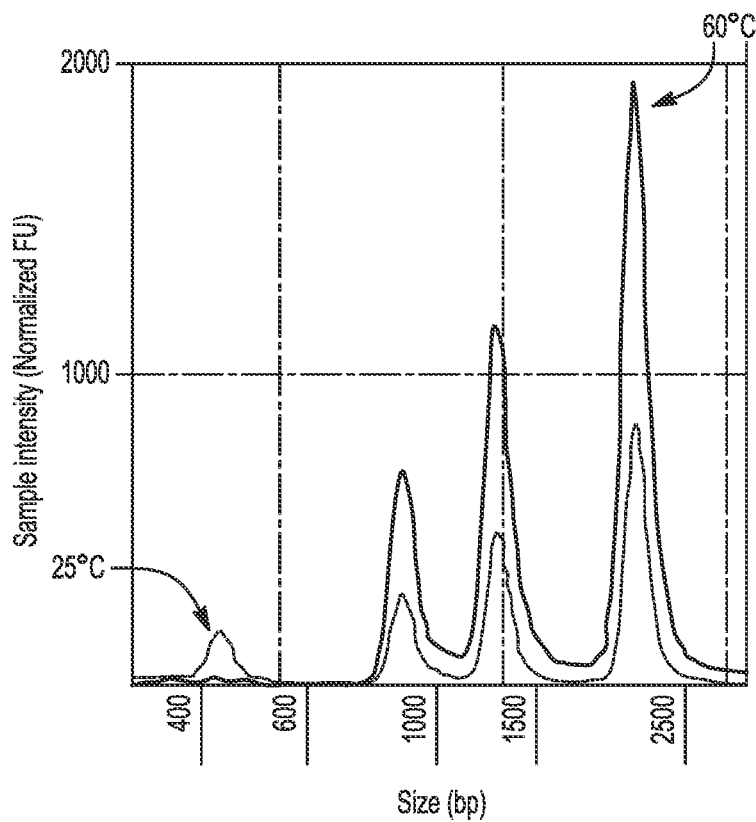
FIG. 9 is a graph depicting the sample intensity (Y-axis, normalized fluorescence units) versus the DNA insert size (X-axis, base pairs) for sample fluids exposed to an example of the purification method disclosed herein at different temperatures.

The TapeStation results for the first supernatant and for the precipitate are shown in FIG. 9 (sample intensity (normalized FU on the Y-axis) versus size (number of base pairs on the X-axis)). The first supernatant had more of the smaller DNA inserts, while the precipitate had more of the larger DNA inserts. These results demonstrate the ability of the method disclosed herein to remove smaller DNA inserts through complexation of the larger DNA inserts with methyl cellulose.

Example 3

One sample fluid (Ex. 1) and one comparative sample fluid (Comp. Ex. 2) were prepared with the PhiX library. Ex. 1 included water and methyl cellulose (1% METHOCEL® E from Dow Chemical Co.) and the PhiX library. Comp. ex. 2 included water and the PhiX library, without any methyl cellulose.

Both Ex. 1 and Comp. ex. 2 were incubated for 5 minutes with heat at 60° C. Ex. 1 and Comp. ex. 2 were then centrifuged and decanted. The respective precipitates were rinsed to remove unbound DNA and were re-suspended in a 1 M TRIS buffer and cooled (to release any bound DNA inserts). Each of the re-suspended solutions was run on an Agilent TapeStation.

Figure 10:
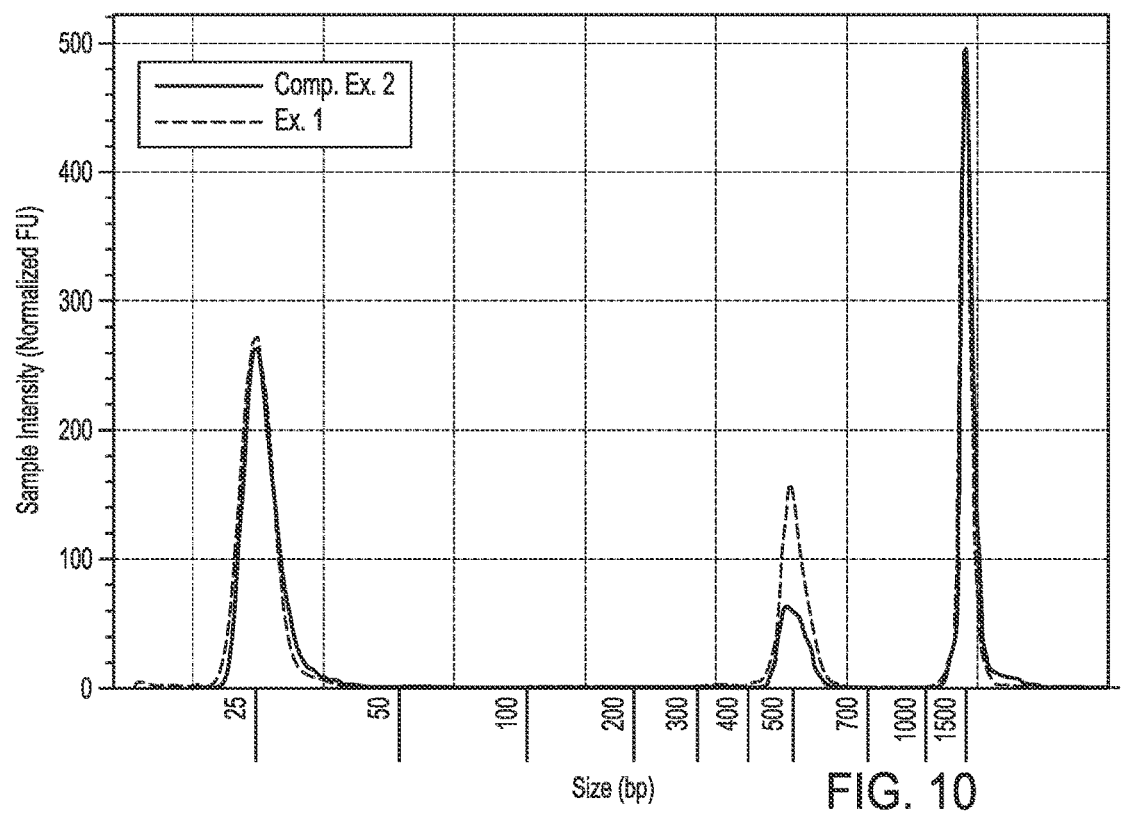
FIG. 10 is a graph depicting the sample intensity (Y-axis, normalized fluorescence units) versus the DNA insert size (X-axis, base pairs) for a control fluid and a sample fluid exposed to an example of the capture method disclosed herein.

The TapeStation results for Ex. 1 and Comp. ex. 2 are shown in FIG. 10 (sample intensity (normalized FU on the Y-axis) versus size (number of base pairs on the X-axis)). Ex. 1 exhibited sharper peaks compared to Comp. ex. 2, thus demonstrating that the methyl cellulose captured the larger DNA inserts. In particular, Comp. ex. 2 had a low broad peak at 500 bp, while Ex. 1 has a much higher and sharper peak. This indicated that Ex. 1 was more concentrated and potentially purified.

The re-suspended libraries from both Ex. 1 and Comp. ex. 2 were subsequently run on an iSeq™ sequencing system (Illumina Inc.) to determine whether methyl cellulose had any detrimental effects on the library itself. While not reproduced herein, the sequencing metrics of Ex. 1 and Comp. ex. 2 were found to be similar and thus confirmed that methyl cellulose did not have any detrimental effects on the library itself.

Example 4

Two additional sample fluids (Ex. 3 and Ex. 4) and one additional comparative sample fluid (Comp. Ex. 5) were prepared with the PhiX library. Ex. 3 included water, methyl cellulose (1% METHOCEL® E from Dow Chemical Co.) and the PhiX library. Ex. 4 included water, methyl cellulose (5% METHOCEL® E from Dow Chemical Co.) and the PhiX library. Comp. ex. 5 included water and the PhiX library, without any methyl cellulose.

Ex. 3, Ex. 4 and Comp. ex. 5 were incubated for 5 minutes with heat at 60° C. Ex. 3, Ex. 4 and Comp. ex. 5 were then centrifuged and decanted. The respective precipitates were rinsed to remove unbound DNA and were re-suspended in a 1 M TRIS buffer and cooled (to release any bound DNA inserts). Each of the re-suspended solutions was run on an Agilent TapeStation.

Figure 11:
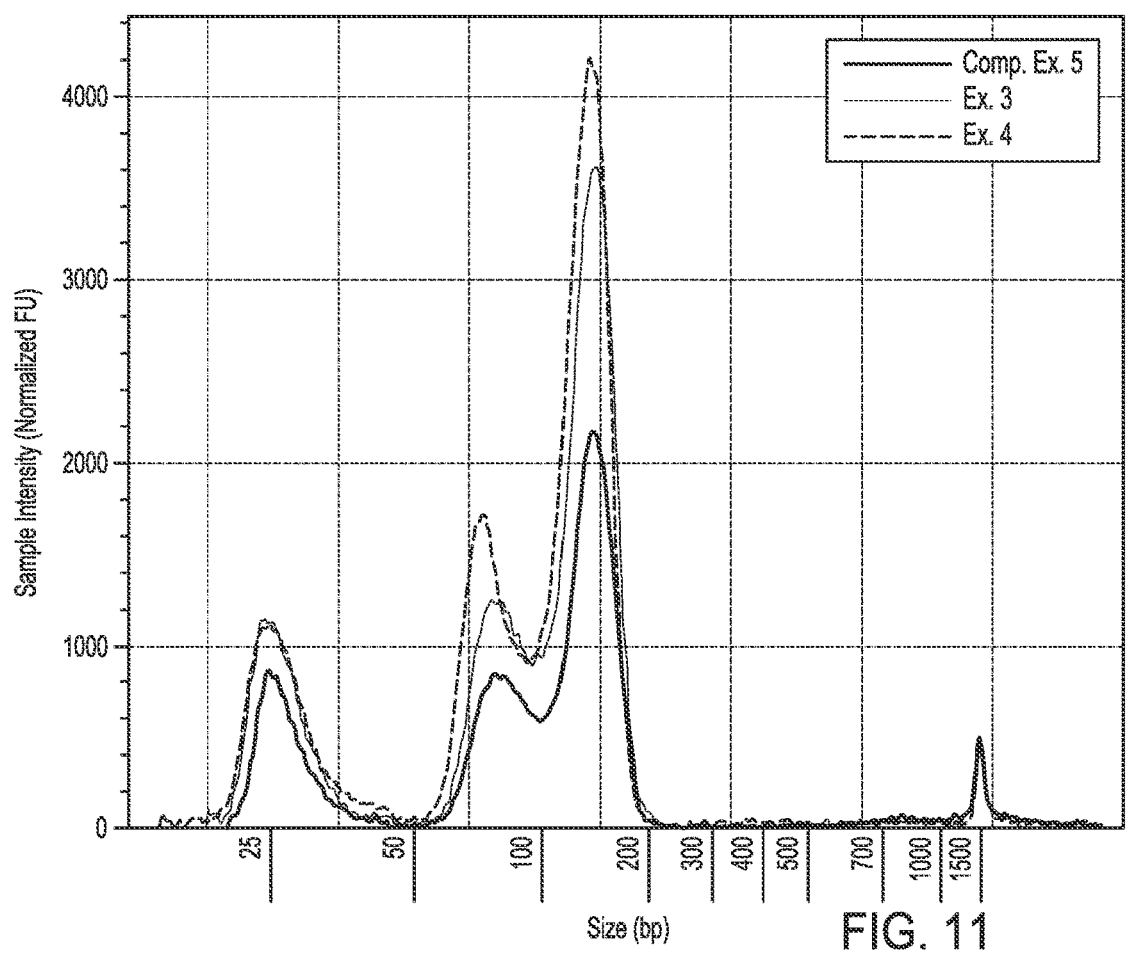
FIG. 11 is a graph depicting the sample intensity (Y-axis, normalized fluorescence units) versus the DNA insert size (X-axis, base pairs) for a control fluid and two sample fluids exposed to an example of the capture method disclosed herein.

The TapeStation results for Ex. 3, Ex. 4 and Comp. ex. 5 are shown in FIG. 11 (sample intensity (normalized FU on the Y-axis) versus size (number of base pairs on the X-axis)). As the methyl cellulose concentration increased (from Comp. ex. 5 to Ex. 3 to Ex. 4) the peaks around 25 bp, 75 bp, and 170 bp became taller and sharper. The results demonstrate that a high concentration of methyl cellulose did not deleteriously affect the capturing efficiency of the polymer.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range of about 400 nm to about 1 μm (1000 nm), should be interpreted to include not only the explicitly recited limits of about 400 nm to about 1 μm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A kit, comprising:
a flow cell assembly including:
a reaction chamber having:
depressions separated by interstitial regions; and
capture primers attached within each of the depressions;
a temperature controlled flow channel in selective fluid communication with an inlet of the reaction chamber;
a filter positioned in the temperature controlled flow channel, the filter i) to block concentrated deoxyribonucleic acid (DNA)-methyl cellulose complexes generated in the temperature controlled flow channel at a first temperature, and ii) to allow passage of concentrated DNA and methyl cellulose released from the complexes in the temperature controlled flow channel at a second temperature;
a bypass line in fluid communication with an inlet of the temperature controlled flow channel and with an outlet of the temperature controlled flow channel;
a first bypass valve to control flow of a sample fluid to the inlet of the temperature controlled flow channel; and
a second bypass valve to control flow of the concentrated DNA and the methyl cellulose to the reaction chamber.

2. The kit as defined in claim 1, further comprising a sample fluid including:
an aqueous carrier;
a DNA sample;
methyl cellulose;
a polymer that is chemically inert to DNA hybridization; and
a salt.

3. The kit as defined in claim 2, wherein the polymer that is chemically inert to DNA hybridization is selected from the group consisting of polyethylene glycol having a weight average molecular weight ranging from about 500 to less than about 200,000, polyvinyl pyrrolidone, polyvinyl alcohol, and combinations thereof.

4. The kit as defined in claim 2, wherein:
the DNA sample is present in the sample fluid at a first molar concentration ranging from about 1 pM to about 1 mM;
the methyl cellulose is present in the sample fluid in an amount ranging from about 0.5 wt % to about 20 wt % based on a total weight of the sample fluid;
the polymer that is chemically inert to DNA hybridization is present in the sample fluid in an amount ranging from greater than 0 wt % to about 20 wt % based on the total weight of the sample fluid; and
the salt is present in the sample fluid at a second molar concentration ranging from greater than 0 M to about 2 M.

5. The kit as defined in claim 2, wherein:
the DNA sample is present in the sample fluid at a first molar concentration ranging from about 1 pM to about 1 mM;
the methyl cellulose is present in the sample fluid in an amount ranging from about 1 wt % to about 5 wt % based on a total weight of the sample fluid;
the polymer that is chemically inert to DNA hybridization is present in the sample fluid in an amount ranging from about 5 wt % to about 16 wt % based on the total weight of the sample fluid; and
the salt is present in the sample fluid at a second molar concentration ranging from 0.4 M to about 2 M.

6. The kit as defined in claim 5, wherein the polymer that is chemically inert to DNA hybridization is polyethylene glycol having a weight average molecular weight ranging from about 500 g/mol to about 1000 g/mol.

7. The kit as defined in claim 5, wherein the salt is sodium chloride.

8. The kit as defined in claim 2, wherein the salt is sodium chloride; sodium bromide; sodium iodide; salts containing potassium, calcium, magnesium, or ammonium cations; and salts containing carbonate, sulfate, phosphate, or nitrate anions.

9. The kit as defined in claim 2, wherein the DNA sample includes cell-free DNA, library DNA, whole genome amplified DNA, or combinations thereof.

10. The kit as defined in claim 2, wherein the DNA sample includes a plurality of differently sized DNA inserts including small DNA inserts having from about 100 bases or base pairs to about 1,000 bases or base pairs and large DNA inserts having more than 1,000 bases or base pairs.

11. The kit as defined in claim 2, wherein the aqueous carrier includes water, a salt solution, or a buffer solution including a tris(hydroxymethyl)aminomethane hydrochloride (TRIS-HCl) buffer, a tris(hydroxymethyl)aminomethane (TRIS) buffer, or a saline sodium citrate (SSC) buffer.

12. The kit as defined in claim 1, wherein at least one surface of the temperature controlled flow channel includes a heating plate.

13. The kit as defined in claim 1, wherein a number of the depressions in a predefined area ranges from about 100 per $mm^2$ to about 50 million per $mm^2$ with each depression having an average pitch ranging from about 50 nm to about 100 μm and an average volume ranging from about $1\times10^{-3}$ μm$^3$ to about 100 μm$^3$.

14. The kit as defined in claim 1, wherein the reaction chamber further has a polymeric hydrogel present within each of the depressions, and wherein the polymeric hydrogel is an acrylamide copolymer.

15. The kit as defined in claim 14, wherein the capture primers are attached to the polymeric hydrogel within each of the depressions.

16. The kit as defined in claim 15, wherein the polymeric hydrogel and the capture primers are not present on the interstitial regions.

* * * * *